(12) United States Patent
Meyer et al.

(10) Patent No.: US 11,771,834 B2
(45) Date of Patent: Oct. 3, 2023

(54) DOSE CLIP ASSEMBLY FOR SYRINGE

(71) Applicant: Gyroscope Therapeutics Limited, Stevenage (GB)

(72) Inventors: Thomas E. Meyer, Philadelphia, PA (US); Tony C. Siebel, Cincinnati, OH (US); Daniel C. Hutchens, Cold Spring, KY (US); Jacob W. Schubert, Bellevue, KY (US)

(73) Assignee: GYROSCOPE THERAPEUTICS LIMITED, London (GB)

( * ) Notice: Subject to any disclaimer, the term of this patent is extended or adjusted under 35 U.S.C. 154(b) by 236 days.

(21) Appl. No.: 17/065,735

(22) Filed: Oct. 8, 2020

(65) Prior Publication Data

US 2021/0106763 A1    Apr. 15, 2021

Related U.S. Application Data

(60) Provisional application No. 62/913,873, filed on Oct. 11, 2019.

(51) Int. Cl.
*A61M 5/315* (2006.01)
*A61F 9/00* (2006.01)
*A61M 5/31* (2006.01)

(52) U.S. Cl.
CPC ....... *A61M 5/31536* (2013.01); *A61F 9/0008* (2013.01); *A61M 5/3137* (2013.01); *A61M 5/31505* (2013.01); *A61M 2210/0612* (2013.01)

(58) Field of Classification Search
CPC ...... A61M 5/31536; A61M 2210/0612; A61M 5/31595; A61M 5/31501; A61M 5/31505;
(Continued)

(56) References Cited

U.S. PATENT DOCUMENTS 2,295,849 A * 9/1942 Kayden ............... A61M 5/2033
604/210
5,115,816 A  5/1992 Lee
(Continued)

FOREIGN PATENT DOCUMENTS

EP          0904792 A2   3/1999
EP          2708254 A1   3/2014
WO     WO 2011/133097 A1  10/2011

OTHER PUBLICATIONS

Wikipedia, "Hinge", <https://en.wikipedia.org/w/index.php?title=Hinge&oldid=917866142> (Year: 2019).*
(Continued)

*Primary Examiner* — Bhisma Mehta
*Assistant Examiner* — Hong-Van N Trinh
(74) *Attorney, Agent, or Firm* — Frost Brown Todd LLP

(57) ABSTRACT

An apparatus includes a first member and a second member. The first member is configured to receive a portion of a syringe barrel and includes a first stop surface. The second member includes a second stop surface. Each stop surface is configured to engage the portion of a plunger to thereby arrest longitudinal movement of the plunger relative to the syringe barrel. The second member is operable to move relative to the first member from a first position to a second position. The second member remains coupled with the first member while in both the first position and the second position. The second stop surface engages the portion of the plunger when the second member is in the first position. The second stop surface does not prevent the portion of the plunger from reaching the first stop surface when the second member is in the second position.

20 Claims, 26 Drawing Sheets

(58) Field of Classification Search
CPC ........ A61M 5/3153; A61M 2005/3154; A61M 2005/3139; A61M 5/3137; A61M 2005/2073; A61M 2005/2403; A61M 2005/2407; A61M 2005/31508; A61M 5/3158; A61M 11/007; A61M 5/31511
See application file for complete search history.

(56) References Cited

U.S. PATENT DOCUMENTS

| | | | |
|---|---|---|---|
| 5,951,526 A * | 9/1999 | Korisch | A61M 15/0026 604/232 |
| 7,413,734 B2 | 8/2008 | Mistry et al. | |
| 2004/0162528 A1 | 8/2004 | Horvath et al. | |
| 2014/0303565 A1* | 10/2014 | Kubo | A61M 3/00 604/208 |
| 2015/0223977 A1 | 8/2015 | Oberkircher et al. | |
| 2015/0351958 A1 | 12/2015 | Contiliano et al. | |
| 2015/0351959 A1 | 12/2015 | Clem et al. | |
| 2016/0074211 A1 | 3/2016 | Ko et al. | |
| 2016/0074212 A1 | 3/2016 | Price et al. | |
| 2016/0074217 A1 | 3/2016 | Price et al. | |
| 2016/0081849 A1* | 3/2016 | Tsai | A61M 5/3137 604/290 |
| 2017/0258988 A1 | 9/2017 | Meyer et al. | |
| 2017/0360605 A1 | 12/2017 | Oberkircher et al. | |
| 2017/0360606 A1 | 12/2017 | Price et al. | |
| 2017/0360607 A1 | 12/2017 | Price et al. | |
| 2019/0247585 A1 | 8/2019 | Gerlett | |

OTHER PUBLICATIONS

International Search Report and Written Opinion dated Feb. 2, 2021, for International Application No. PCT/IB2020/000836, 19 pages.

* cited by examiner

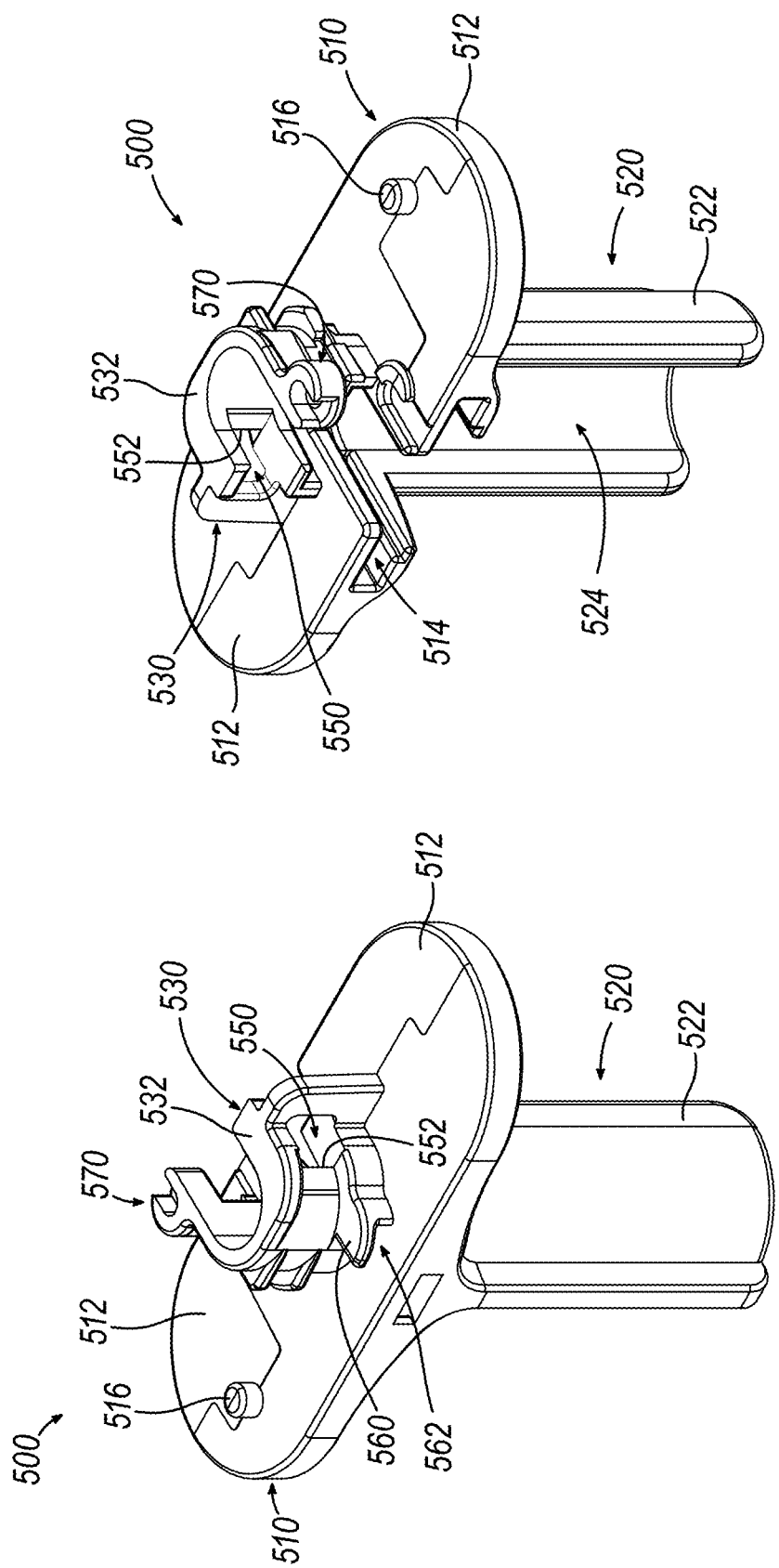

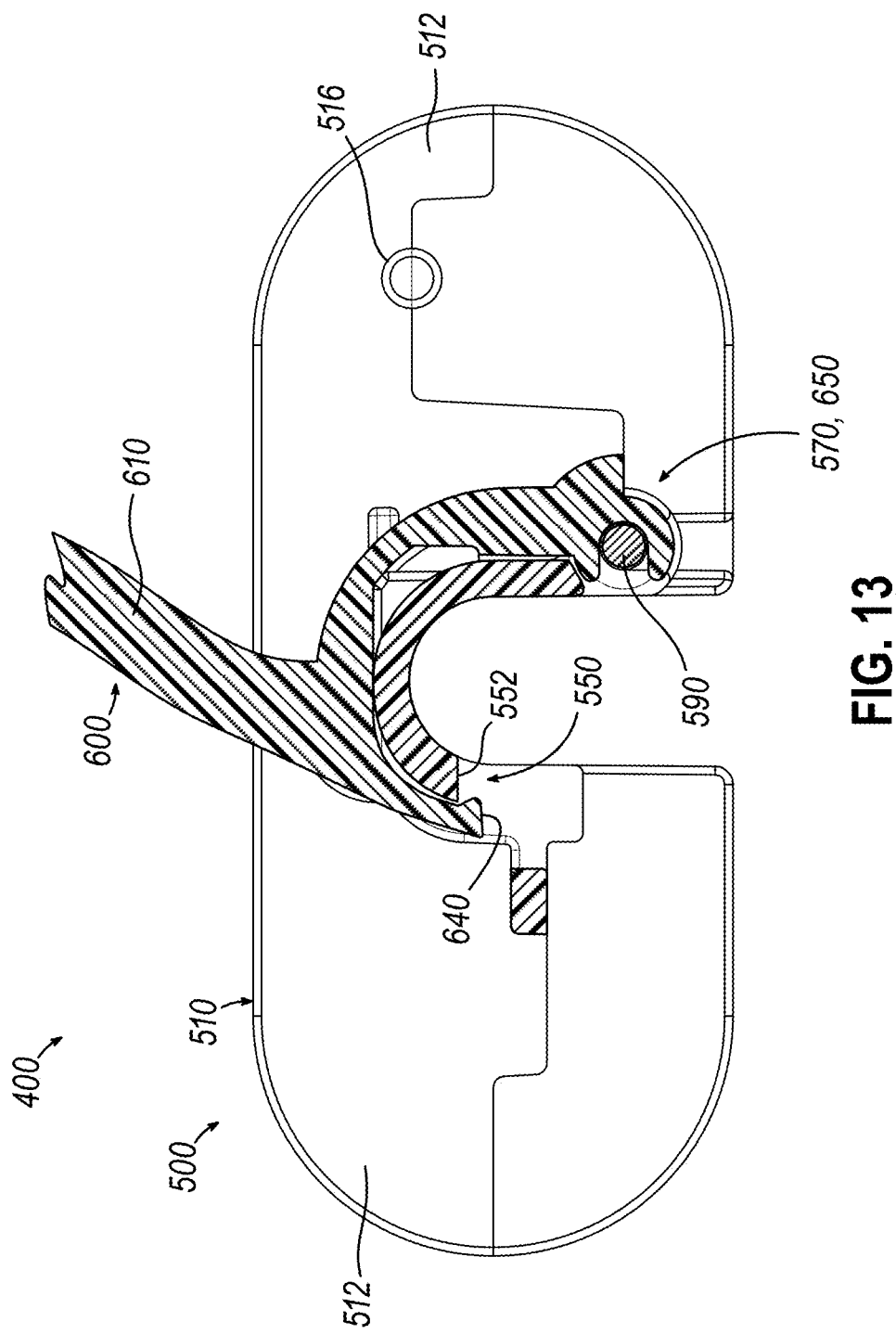

DOSE CLIP ASSEMBLY FOR SYRINGE

PRIORITY

This application claims priority to U.S. Provisional Pat. App. No. 62/913,817, entitled "Dose Clip Assembly for Syringe," filed Oct. 11, 2019, the disclosure of which is incorporated by reference herein.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and, in some cases, may disappear as well. It may therefore be desirable to provide treatment for macular degeneration to prevent or reverse the loss of vision caused by macular degeneration. In some cases, it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8 depicts a perspective view of a lower member of the dose clip assembly of FIG. 5;

FIG. 9 depicts another perspective view of the lower member of FIG. 8;

FIG. 13 depicts a cross-sectional view of the dose clip assembly of FIG. 5, taken along line 13-13 of FIG. 5;

Figure 1:
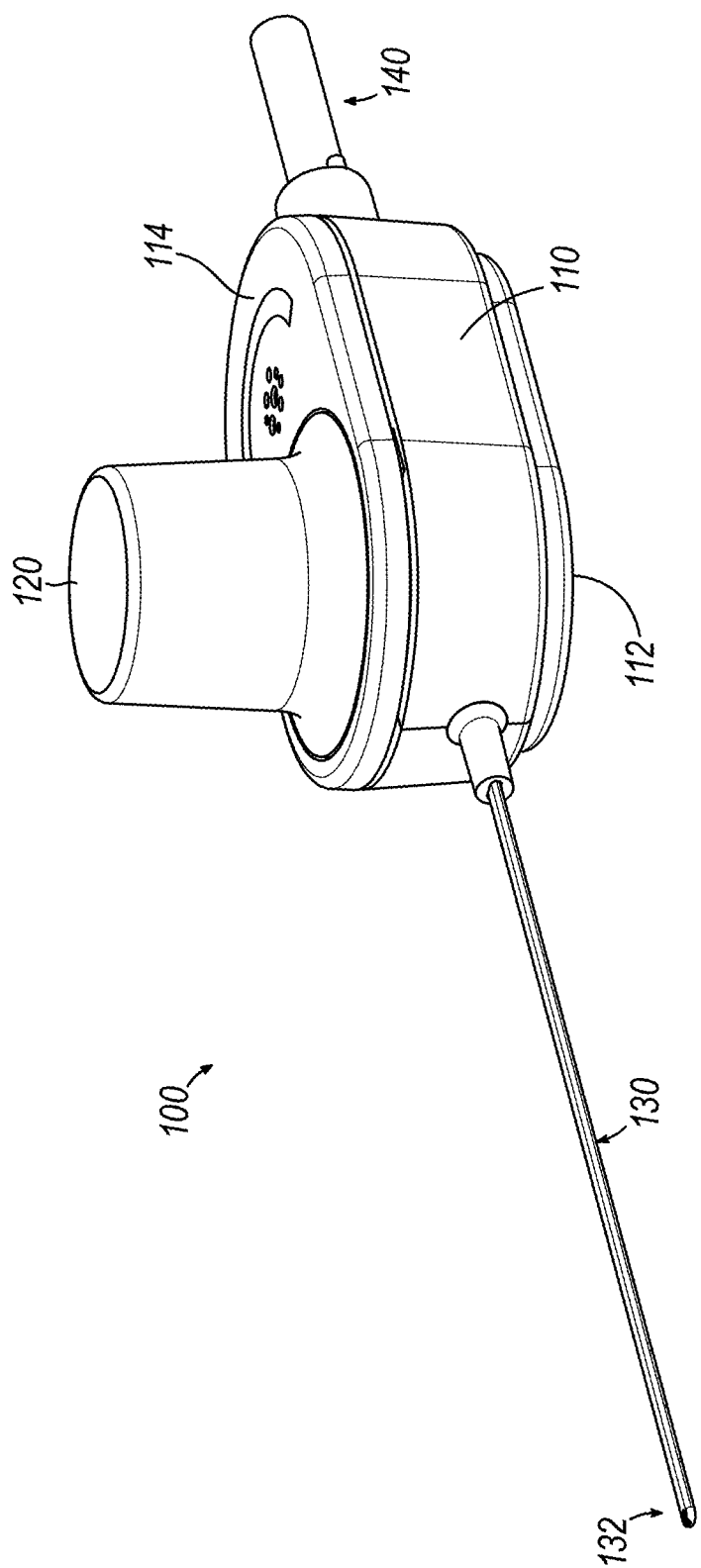
FIG. 1 depicts a perspective view of an example of an instrument for subretinal administration of a therapeutic agent from a suprachoroidal approach.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Instrument for Subretinal Administration of Therapeutic Agent

FIG. 1 shows an example of an instrument (100) that is configured for use in a procedure for the subretinal administration of a therapeutic agent to an eye of a patient from a suprachoroidal approach. Instrument (100) comprises a body (110) and a flexible cannula (130) extending distally from body (110). Cannula (130) of the present example has a generally rectangular cross section, though any other suitable cross-sectional profile (e.g., elliptical, etc.) may be used. The cross-sectional profile of cannula (130) is configured to enable cannula (130) to be passed atraumatically along the suprachoroidal space, as will be described in greater detail below. Cannula (130) is generally configured to support a needle (150) that is slidable within cannula (130), as will be described in greater detail below.

Figure 2A:
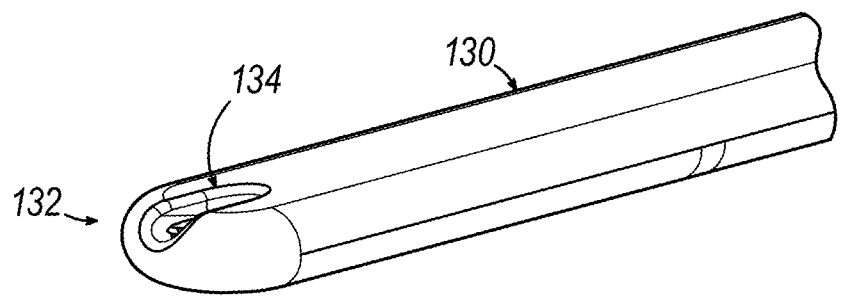
FIG. 2A depicts a perspective view of the distal end of a cannula of the instrument of FIG. 1, with a needle retracted in the cannula.
Figure 2B:
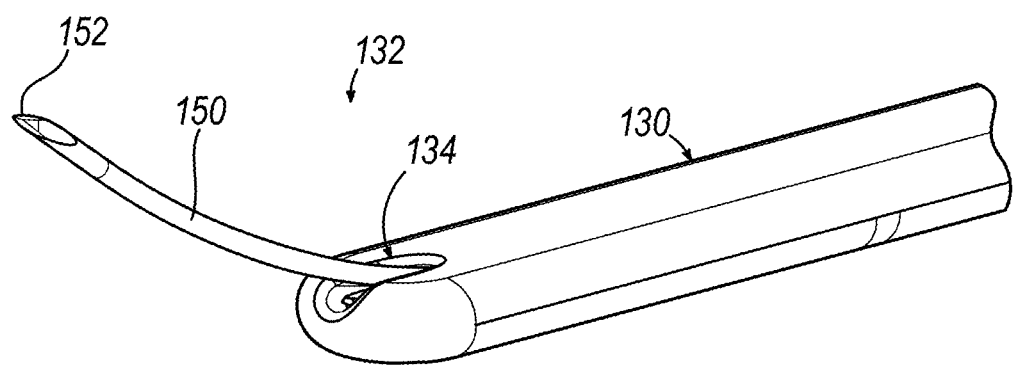
FIG. 2B depicts a perspective view of the distal end of a cannula of FIG. 2A, with a needle extending from the cannula.

In the present example, cannula (130) comprises a flexible material such as Polyether block amide (PEBA). Of course, any other suitable material or combination of materials may be used. Also in the present example, cannula (130) has a cross-sectional profile dimension of approximately 1.6 mm (width) by approximately 0.6 mm (height), with a length of approximately 80 mm. Alternatively, any other suitable dimensions may be used. Cannula (130) of the present example is flexible enough to conform to specific structures and contours of the patient's eye, yet cannula (130) has sufficient column strength to permit advancement of cannula (130) between the sclera and choroid of patient's eye without buckling. As best seen in FIGS. 2A-2B, cannula (130) includes a transversely oriented opening (134) at the distal end (132) of cannula (130). Distal end (132) is atraumatic such that distal end (132) is configured to provide separation between the sclera and choroid layers, as will be described in greater detail below, to thereby enable cannula (130) to be advanced between such layers while not inflicting trauma to the sclera or choroid layers.

By way of example only, cannula (130) may be configured and operable in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2017/0360607, entitled "Apparatus and Method to From Entry Bleb for Subretinal Delivery of Therapeutic Agent," published Dec. 21, 2017, the disclosure of which is incorporated by reference herein; and/or U.S. Pub. No. 2017/0360606, entitled "Injection Device for Subretinal Delivery of Therapeutic Agent," published Dec. 21, 2017, the disclosure of which is incorporated by reference herein.

As shown in FIG. 2B, needle (150) may be advanced distally to protrude from opening (134). Needle (150) of the present example has a sharp distal tip (152) and defines a lumen (not shown). Distal tip (152) of the present example has a lancet configuration. In some other versions, distal tip (152) has a tri-bevel configuration or any other configuration as described in U.S. Pub. No. 2015/0223977, entitled "Method and Apparatus for Subretinal Administration of Therapeutic Agent," published Aug. 13, 2015, the disclosure of which is incorporated by reference herein. Still other suitable forms that distal tip (152) may take will be apparent to those skilled in the art in view of the teachings herein.

Needle (150) of the present example comprises a stainless steel hypodermic needle that is sized to deliver and aspirate fluids while being small enough to minimize incidental trauma as needle (150) penetrates tissue structures of the patient's eye, as will be described in greater detail below. While stainless steel is used in the present example, any other suitable material(s) may be used, including but not limited to nitinol, etc.

By way of example only, needle (150) may be 35 gauge with a 100 μm inner diameter, although other suitable sizes may be used. For instance, the outer diameter of needle (150) may fall within the range of 27 gauge to 45 gauge; or more particularly within the range of 30 gauge to 42 gauge; or more particularly within the range of 32 gauge to 39 gauge. As another merely illustrative example, the inner diameter of needle (150) may fall within the range of approximately 50 μm to approximately 200 μm; or more particularly within the range of approximately 50 μm to approximately 150 μm; or more particularly within the range of approximately 75 μm to approximately 125 μm.

In some versions, a needle guide (not shown) is disposed within cannula (130) to guide needle (150) along a predefined angle as needle (150) exits through opening (134). By way of example only, the exit angle for needle (150) may be within the range of approximately 5° to approximately 30° relative to the longitudinal axis of cannula (130); or more particularly within the range of approximately 5° to approximately 20° relative to the longitudinal axis of cannula (130); or more particularly within the range of approximately 5° to approximately 10° relative to the longitudinal axis of cannula (130); or more particularly within the range of approximately 7° and approximately 9° relative to the longitudinal axis of cannula (130). In addition to or in lieu of providing a needle guide within cannula (130), needle (150) may be resiliently biased to assume a bent configuration to thereby provide an exit angle that varies based on the extent to which needle (130) is advanced distally relative to cannula (130). By way of example only, needle (150) may include a preformed bend in accordance with at least some of the teachings of U.S. Pub. No. 2017/0258988, entitled "Apparatus for Subretinal Administration of Therapeutic Agent via a Curved Needle," published Sep. 14, 2017, the disclosure of which is incorporated by reference herein.

In the present example, the generally rectangular, generally elliptical, or otherwise generally flat cross-sectional profile of cannula (130) prevents cannula (130) from rotating about the longitudinal axis of cannula (130) when cannula (130) is disposed in the suprachoroidal space as will be described in greater detail below. This provides a consistent and predictable orientation of opening (134), thereby providing a consistent and predictable exit path for needle (150) when needle (150) is advanced distally relative to cannula (130) as will be described in greater detail below.

As shown in FIG. 1, instrument (100) of the present example further comprises an actuation knob (120) located at a top portion (114) of body (110). Actuation knob (120) is rotatable relative to body (110) to thereby selectively translate needle (150) longitudinally relative to cannula (130). In particular, actuation knob (120) is rotatable in a first angular direction to drive needle (150) distally relative to cannula (130); and in a second angular direction to drive needle (150) proximally relative to cannula (130). By way of example only, instrument (100) may provide such functionality through knob (120) in accordance with at least some of the teachings of U.S. Pub. No. 2017/0360606, the disclosure of which is incorporated by reference herein; and/or U.S. Pub. No. 2017/0360607, the disclosure of which is incorporated by reference herein. Other suitable ways in which rotary motion of knob (120) may be converted to linear translation of needle (150) will be apparent to those skilled in the art in view of the teachings herein. Similarly, other suitable ways in which needle (150) may be actuated (150) longitudinally relative to cannula (130) will be apparent to those skilled in the art in view of the teachings herein.

As also shown in FIG. 1, a conduit assembly (140) extends proximally from body (110). Conduit assembly (140) is configured to contain one or more fluid conduits (not shown) that are in fluid communication with needle (150). Such fluid conduits may comprise one or more flexible tubes, etc. In some versions, conduit assembly (140) also contains one or more wires. By way of example only, such wires may provide communication of data signals from one or more sensors in body (110) to a processor that is remote from instrument (100). Such a configuration and operability may be carried out in accordance with at least some of the teachings of U.S. Pub. No. 2017/0360606, the disclosure of which is incorporated by reference herein; and/or U.S. Pub. No. 2017/0360607, the disclosure of which is incorporated by reference herein. By way of further example only, such wires may provide communication of electrical power to one or more electrically powered components in body (110). Various suitable ways in which electrical power and/or signals may be implemented through one or more wires in conduit assembly (140) and one or more electrically associated components in body (110) will be apparent to those skilled in the art in view of the teachings herein. Alternatively, some versions of conduit assembly (140) may lack wires altogether; and body (110) may lack sensors, electrically powered components, etc.

The features and operability of instrument (100) may be varied in numerous ways. In addition, instrument (100) may be modified in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein. Other suitable modifications will be apparent to those skilled in the art in view of the teachings herein.

Figure 3:
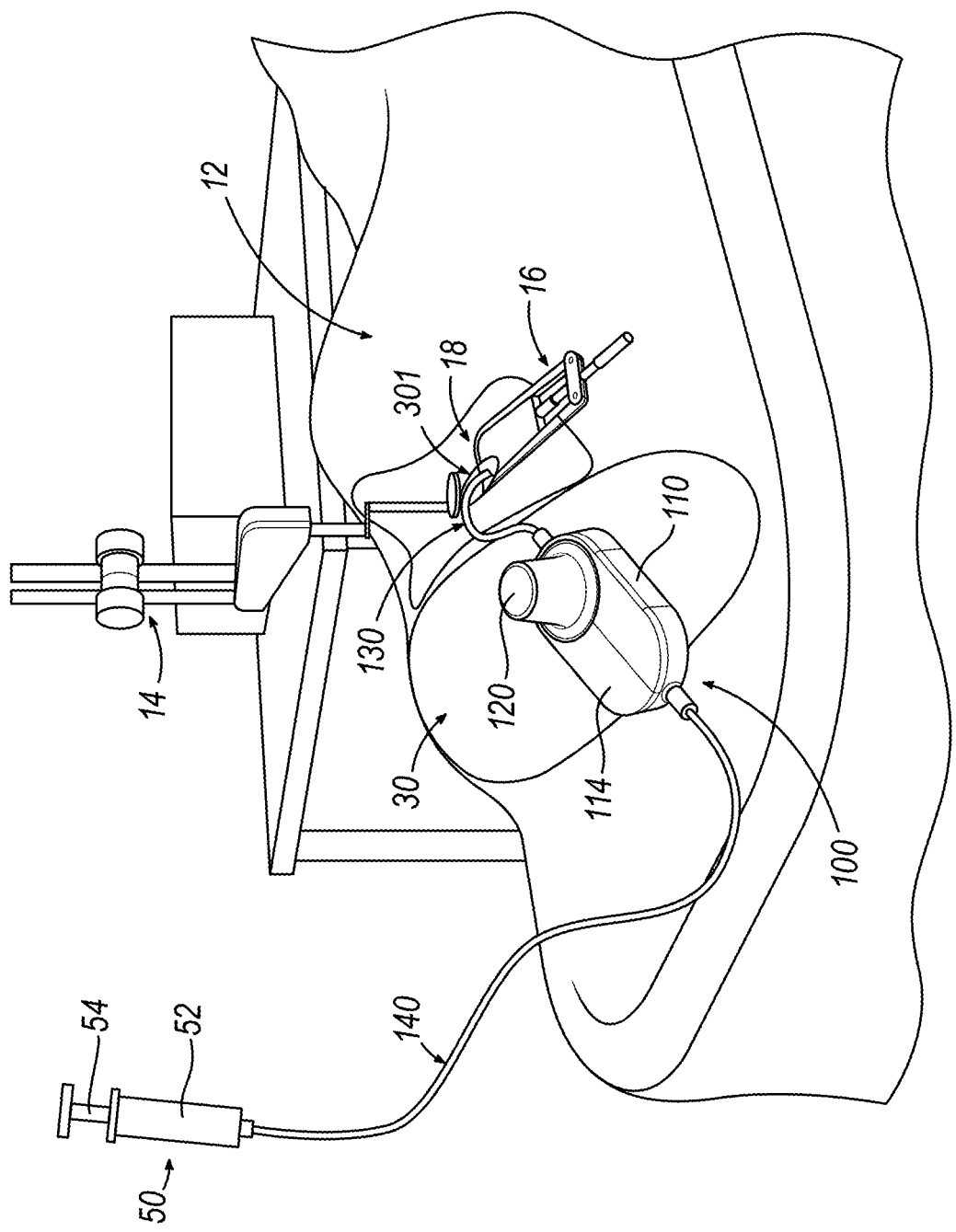
FIG. 3 depicts a perspective view of the instrument of FIG. 1, mounted near a patient, in combination with other equipment.

II. Procedure for Delivery of a Therapeutic Agent to Subretinal Space from a Suprachoroidal Approach FIG. 3 shows a scenario where instrument (100) is positioned in relation to a patient. In this example, a drape (12) is disposed over the patient, with an opening (18) formed in drape (12) near the patient's eye (301). A speculum (16) is used to keep the eye (301) open. A fixture (14) is positioned adjacent to the eye (301). Fixture (14) may be used to secure instrumentation, such as a viewing scope, relative to the patient. A magnetic pad (30) is adhered to drape (12) near the opening (18) adjacent to the eye (301). Instrument (100) is placed on magnetic pad (30) and is removably secured thereto via magnetic attraction. In the present example, one or more permanent magnets (not shown) are positioned within body (110) near bottom portion (112); and these magnets are magnetically attracted to one or more ferrous elements (not shown) contained within magnetic pad (30). By way of example only, these magnets and magnetic pad (30) may be configured in accordance with at least some of the teachings of U.S. Pub. No. 2017/0360606, the disclosure of which is incorporated by reference herein. Instrument (100) is oriented to enable insertion of flexible cannula (130) of instrument (100) into the eye (301). An example of a process for inserting and positioning cannula (130) in the eye (301) is described in greater detail below with reference to FIGS. 4A-4F.

As also shown in FIG. 3, conduit assembly (140) may be coupled with a fluid source such as a conventional syringe (50). Syringe (50) of this example comprises a barrel (52) and a plunger (54). Barrel (52) is in fluid communication with needle (150) via conduit assembly (140). While only one syringe (50) is coupled with conduit assembly (140) in this example, two or more syringes (50) may be coupled with conduit assembly (140) in other scenarios. Two or more syringes (50) may be coupled with conduit assembly (140) via one or more "Y" fittings, a manifold, or any other structure as will be apparent to those skilled in the art in view of the teachings herein.

FIGS. 4A-4G show an example of a procedure that may be carried out using the above-described equipment, to deliver a therapeutic agent to the subretinal space of the eye (301) from a suprachoroidal approach using. By way of example only, the method described herein may be employed to treat macular degeneration and/or other ocular conditions. Although the procedure described herein is discussed in the context of the treatment of age-related macular degeneration, no such limitation is intended or implied. For instance, in some alternative procedures, the same techniques described herein may be used to treat retinitis pigmentosa, diabetic retinopathy, and/or other ocular conditions. Additionally, the procedure described herein may be used to treat either dry or wet age-related macular degeneration, among other conditions.

Figure 4A:
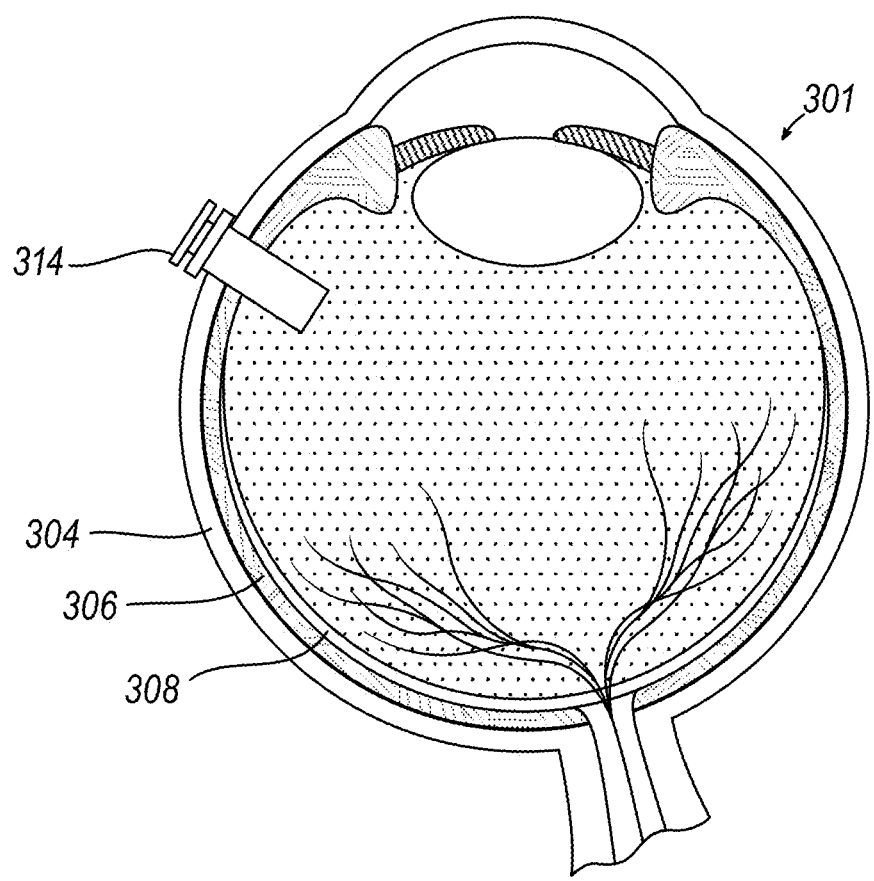
FIG. 4A depicts a cross-sectional side view of an eye of a patient.

In the present example, the procedure begins by an operator immobilizing tissue surrounding a patient's eye (301) (e.g., the eyelids) using an instrument such as speculum (16), and/or any other instrument suitable for immobilization. While immobilization described herein with reference to tissue surrounding eye (301), eye (301) itself may remain free to move. Once the tissue surrounding eye (301) has been immobilized, an eye chandelier port (314) is inserted into eye (301), as shown in FIG. 4A, to provide intraocular illumination when the interior of eye (301) is viewed through the pupil. In the present example, eye chandelier port (314) is positioned in the inferior medial quadrant such that a superior temporal quadrant sclerotomy may be performed. Eye chandelier port (314) is positioned to direct light onto the interior of eye (301) to illuminate at least a portion of the retina (308) (e.g., including at least a portion of the macula). As will be understood, such illumination corresponds to an area of eye (301) that is being targeted for delivery of therapeutic agent.

In the present example, only chandelier port (314) is inserted at the stage shown in FIG. 4A, without yet inserting an optical fiber (315) into port (314). In some other versions, an optical fiber (315) may be inserted into chandelier port (314) at this stage. In either case, a microscope may optionally be utilized to visually inspect the eye to confirm proper positioning of eye chandelier port (314) relative to the target site. Although FIG. 4A shows a certain positioning of eye chandelier port (314), eye chandelier port (314) may have any other suitable positioning as will be apparent to those skilled in the art in view of the teachings herein.

Once eye chandelier port (314) has been positioned, the sclera (304) may be accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device.

Figure 4B:
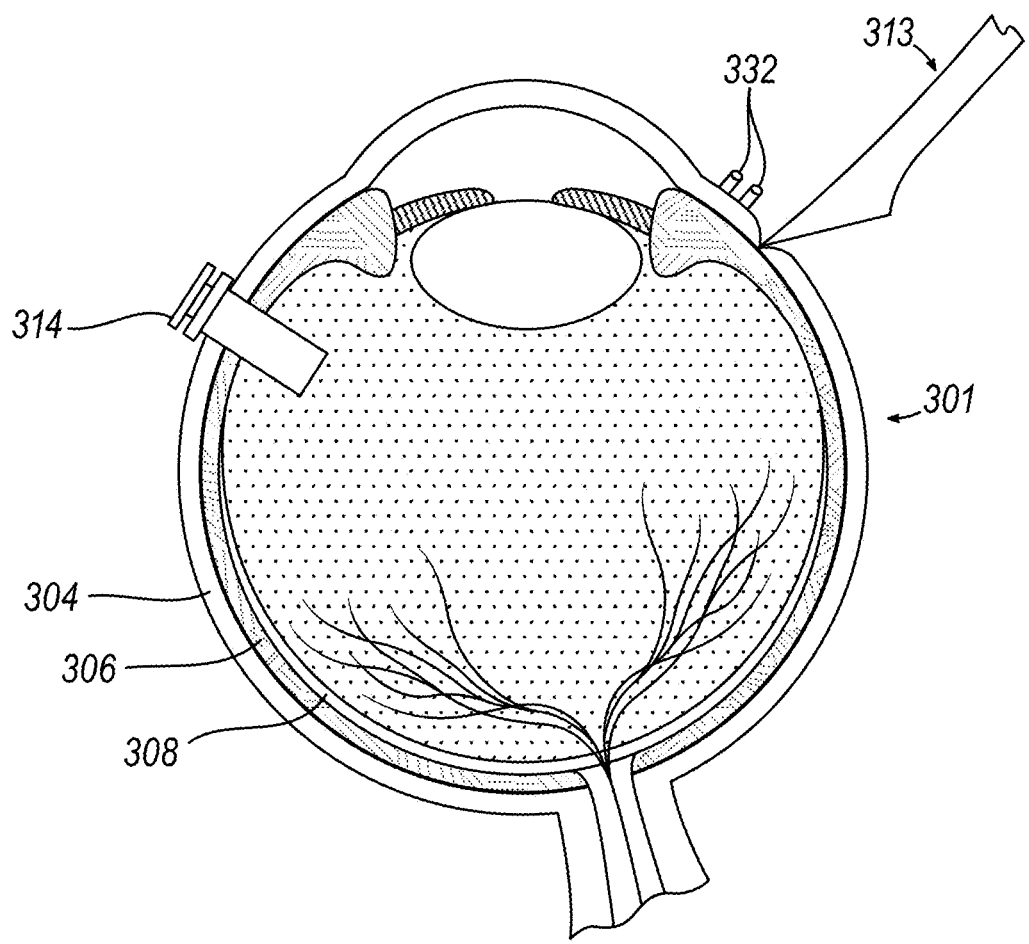
FIG. 4B depicts a cross-sectional side view of the eye of FIG. 4A, with a suture loop attached to the eye, and with a sclerotomy being performed.

A template may then be used to mark the eye (20), as described in U.S. Pub. No. 2015/0223977, the disclosure of which is incorporated by reference herein; and/or U.S. Pub. No. 2017/0360605, entitled "Guide Apparatus for Tangential Entry into Suprachoroidal Space," published Dec. 21, 2017, the disclosure of which is incorporated by reference herein. The operator may then use a visual guide created using the template to attach a suture loop assembly (332) and to perform a sclerotomy, as shown in FIG. 4B, using a conventional scalpel (313) or other suitable cutting instrument. By way of example only, suture loop assembly (70) may be formed in accordance with at least some of the teachings of U.S. Pub. No. 2015/0223977, the disclosure of which is incorporated by reference herein. Alternatively, in lieu of suture loop assembly (70), the operator may install a guide tack in accordance with at least some of the teachings of U.S. Pub. No. 2017/0360605, the disclosure of which is incorporated by reference herein.

The sclerotomy procedure forms a small incision through sclera (304) of eye (301). The sclerotomy is performed with particular care to avoid penetration of the choroid (306). Thus, the sclerotomy procedure provides access to the space between sclera (304) and choroid (306). Once the incision is made in eye (301), a blunt dissection may optionally be performed to locally separate sclera (304) from choroid (306). Such a dissection may be performed using a small blunt elongate instrument, as will be apparent to those skilled in the art in view of the teachings herein.

Figure 4C:
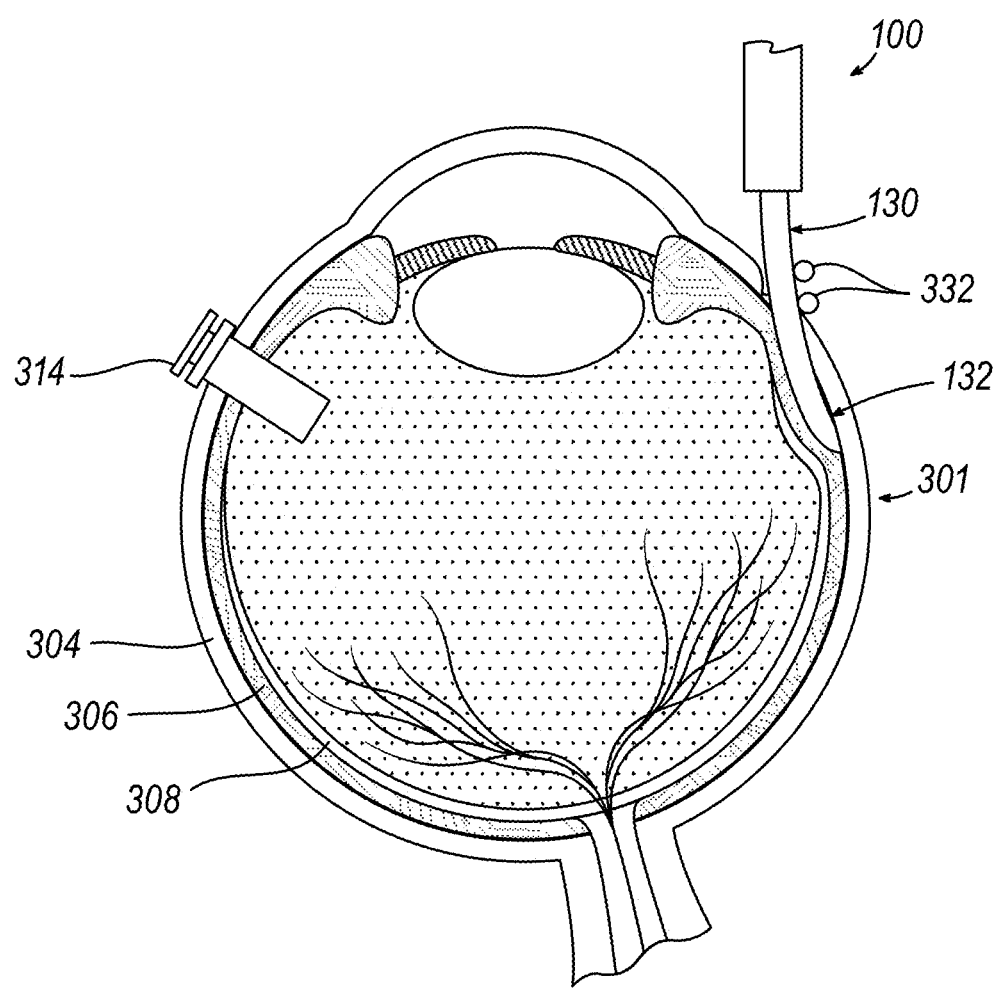
FIG. 4C depicts a cross-sectional side view of the eye of FIG. 4A, with the cannula of FIG. 2A being inserted through the sclerotomy opening and in between the sclera and choroid of the eye.

With the sclerotomy procedure performed, an operator may insert cannula (130) of instrument (100) through incision (316) and into the space between sclera (304) and choroid (306). As can be seen in FIG. 4C, cannula (130) is directed through suture loop assembly (332) and into the incision. Suture loop assembly (332) may stabilize cannula (130) during insertion. Additionally, suture loop assembly (332) maintains cannula (130) in a generally tangential orientation relative to the incision. Such tangential orientation may reduce trauma as cannula (130) is guided through the incision. As cannula (130) is inserted into the incision through suture loop assembly (332), an operator may use forceps or other instruments to further guide cannula (130) along an atraumatic path. Of course, use of forceps or other instruments is merely optional, and may be omitted in some examples. As noted above, a guide tack (or other device) may be used in lieu of suture loop assembly (332). Cannula (130) is advanced until distal end (132) is positioned near the targeted region of the subretinal space, on the opposite side of the choroid (306). Various suitable ways of visualizing distal end (132) to thereby observe proper positioning of distal end (132) will be apparent to those skilled in the art in view of the teachings herein.

Although not shown, in some examples, cannula (130) may include one or more markers on the surface of cannula (130) to indicate various depths of insertion. While merely optional, such markers may be desirable to aid an operator in identifying the proper depth of insertion as cannula (130) is guided along an atraumatic path. For instance, the operator may visually observe the position of such markers in relation to suture loop assembly (332) and/or in relation to the incision in the sclera (304) as an indication of the depth to which cannula (130) is inserted in eye (301). By way of example only, one such marker may correspond to an approximately 6 mm depth of insertion of cannula (130).

Figure 4D:
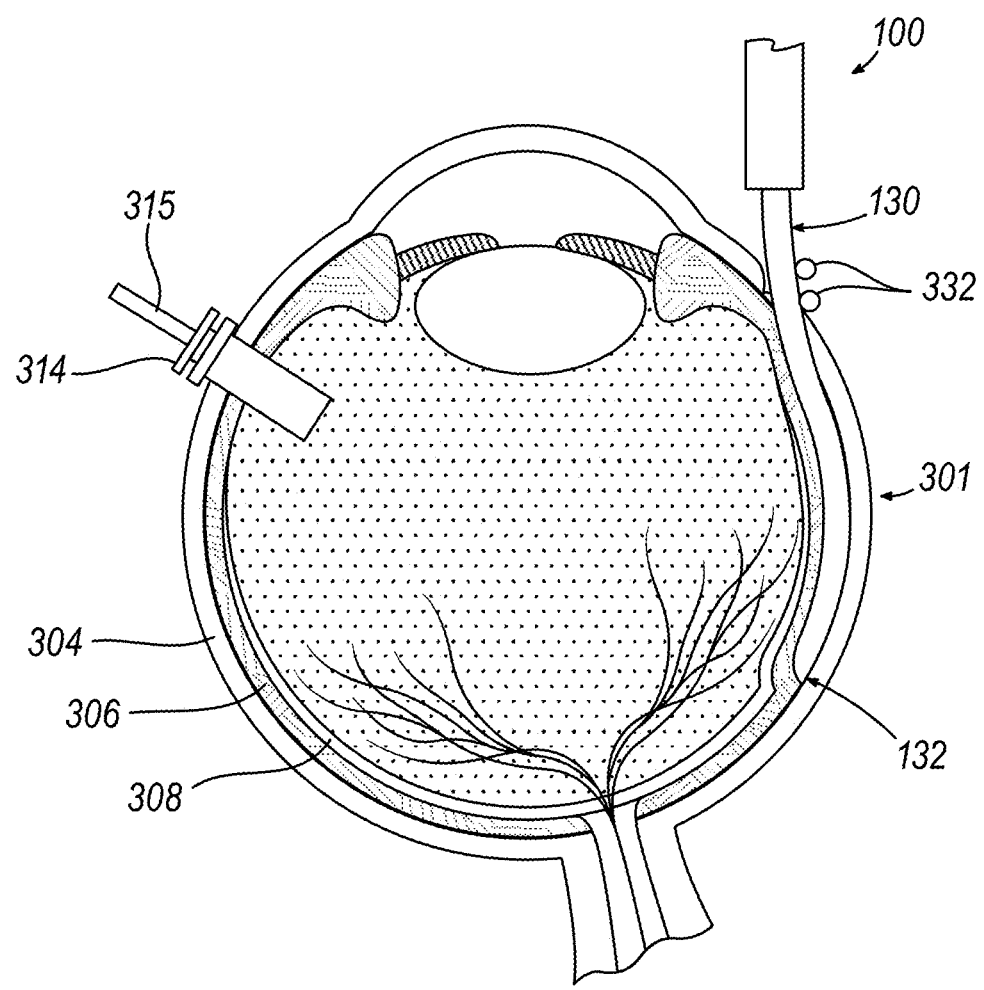
FIG. 4D depicts a cross-sectional side view of the eye of FIG. 4A, with the distal end of the cannula being positioned adjacent to a target location.

As shown in FIG. 4D, once cannula (130) is at least partially inserted into eye (301), an operator may insert an optical fiber (315) into eye chandelier port (314) if the fiber (315) had not yet been inserted at this stage. With eye chandelier port (314) in place and assembled with optical fiber (315), an operator may activate eye chandelier port (314) by directing light through optical fiber (315) to provide illumination of eye (301) and thereby visualize the interior of eye (301). Further adjustments to the positioning of cannula (130) may optionally be made at this point to ensure proper positioning relative to the area of geographic atrophy of retina (308). In some instances, the operator may wish to rotate the eye (301), such as by pulling on suture loop assembly (332), to direct the pupil of the eye (301) toward the operator in order to optimize visualization of the interior of the eye (301) via the pupil.

FIGS. 4C-4D show cannula (130) as it is guided between sclera (304) and choroid (306) to position distal end (132) of cannula (130) at the delivery site for the therapeutic agent. In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. By way of example only, the operator may rely on direct visualization through a microscope directed through the pupil of eye (301) as cannula (130) is being advanced through the range of motion shown in FIGS. 4C-4D, with illumination provided through fiber (315) and port (314). Cannula (130) may be at least partially visible through a retina (308) and choroid (306) of eye (301). Visual tracking may be enhanced in versions where an optical fiber is used to emit visible light through the distal end of cannula (130).

Figure 4E:
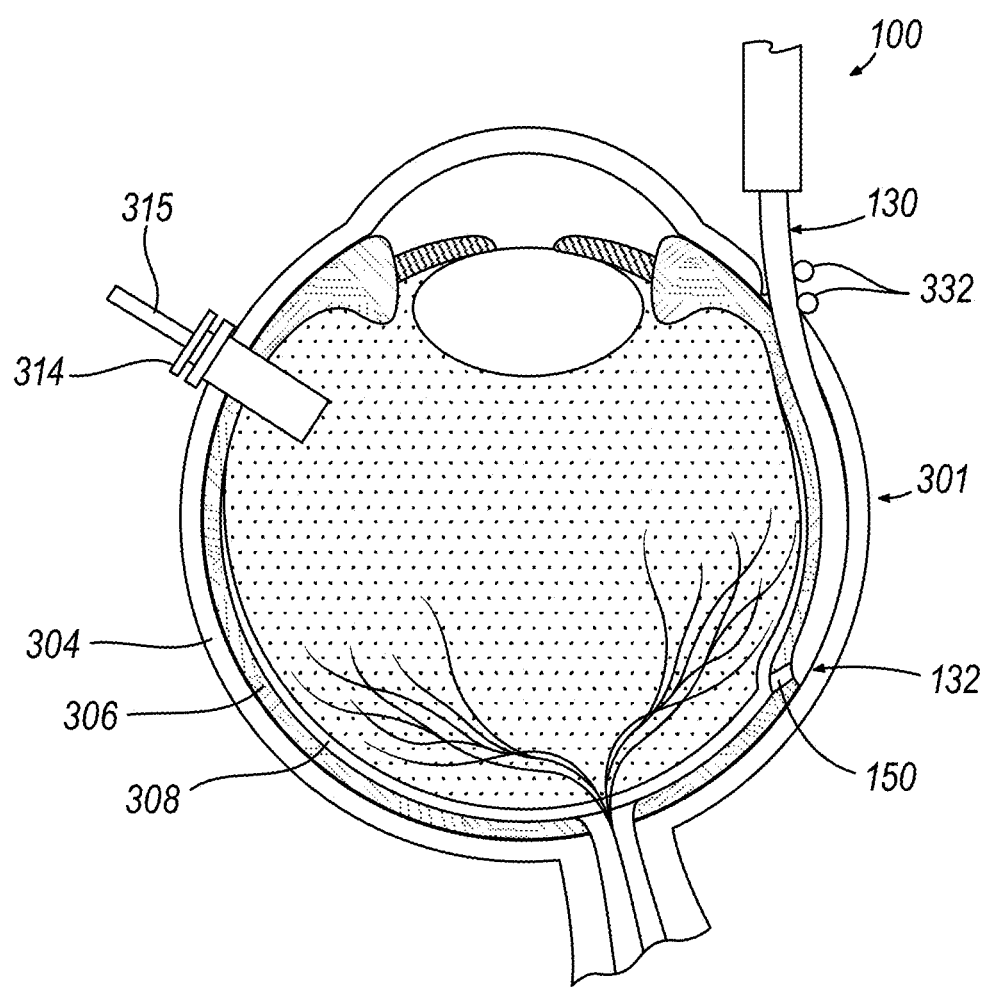
FIG. 4E depicts a cross-sectional side view of the eye of FIG. 4A, with the needle of FIG. 2B being advanced through the choroid to access the subretinal space at the target location.

Once cannula (130) has been advanced to the delivery site as shown in FIG. 4D, an operator may advance needle (150) of instrument (100) as described above by actuating knob (120). As can be seen in FIG. 4E, needle (150) is advanced relative to cannula (130) such that needle (150) pierces through choroid (306) without penetrating retina (308). Immediately prior to penetrating choroid (306), needle (150) may appear under direct visualization as "tenting" the surface of choroid (306). In other words, needle (150) may deform choroid (306) by pushing upwardly on choroid (306), providing an appearance like a tent pole deforming the roof of a tent. Such a visual phenomenon may be used by an operator to identify whether choroid (306) is about to be pierced and the location of any eventual piercing. The particular amount of needle (150) advancement sufficient to initiate "tenting" and subsequent piercing of choroid (306) may be of any suitable amount as may be determined by a number of factors such as, but not limited to, general patient anatomy, local patient anatomy, operator preference, and/or other factors. As described above, an example of a range of needle (150) advancement may be between approximately 0.25 mm and approximately 10 mm; or more particularly between approximately 2 mm and approximately 6 mm.

Figure 4F:
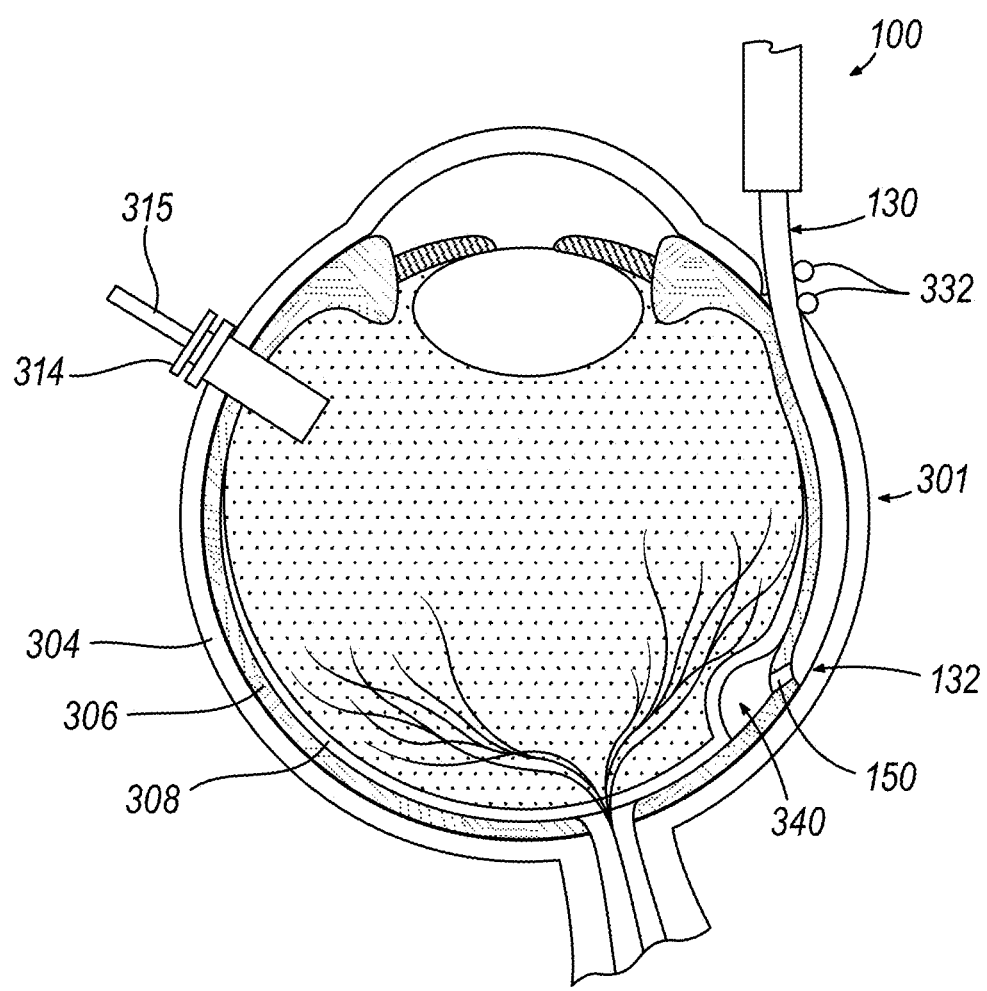
FIG. 4F depicts a cross-sectional side view of the eye of FIG. 4A, with the needle of FIG. 2B dispensing a first volume of leading bleb fluid to provide separation between a region of the retina and the choroid at the target location.

In the present example, after the operator has confirmed that needle (150) has been properly advanced by visualizing the tenting effect described above, the operator infuses a balanced salt solution (BSS) or other similar solution as needle (150) is advanced relative to cannula (130). Such a BSS may form a leading bleb (340) ahead of needle (150) as needle (150) is advanced through choroid (306). Leading bleb (340) may be desirable for two reasons. First, as shown in FIG. 4F, leading bleb (340) may provide a further visual indicator to an operator to indicate when needle (150) is properly positioned at the delivery site. Second, leading bleb (340) may provide a barrier between needle (150) and retina (308) once needle (150) has penetrated choroid (306). Such a barrier may push the retinal wall outwardly, thereby minimizing the risk of retinal perforation as needle (150) is advanced to the delivery site. In some versions, a foot pedal is actuated in order to drive leading bleb (340) out from needle (150). Alternatively, other suitable features that may be used to drive leading bleb (340) out from needle (150) will be apparent to those skilled in the art in view of the teachings herein.

Once the operator visualizes leading bleb (340), the operator may cease infusion of BSS, leaving a pocket of fluid as can be seen in FIG. 4F. Next, a therapeutic agent (342) may be infused by actuating syringe (50) or some other fluid delivery device as described in various references cited herein. The delivered therapeutic agent (342) may be any suitable therapeutic agent configured to treat an ocular condition. Some merely illustrative examples of suitable therapeutic agents may include, but are not necessarily limited to, drugs having smaller or large molecules, therapeutic cell solutions, certain gene therapy solutions, tissue plasminogen activators, and/or any other suitable therapeutic agent as will be apparent to those skilled in the art in view of the teachings herein. By way of example only, the therapeutic agent (342) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. In addition to, or as an alternative to, being used to deliver a therapeutic agent (342), instrument (100) and variations thereof may be used to provide drainage and/or perform other operations.

Figure 4G:
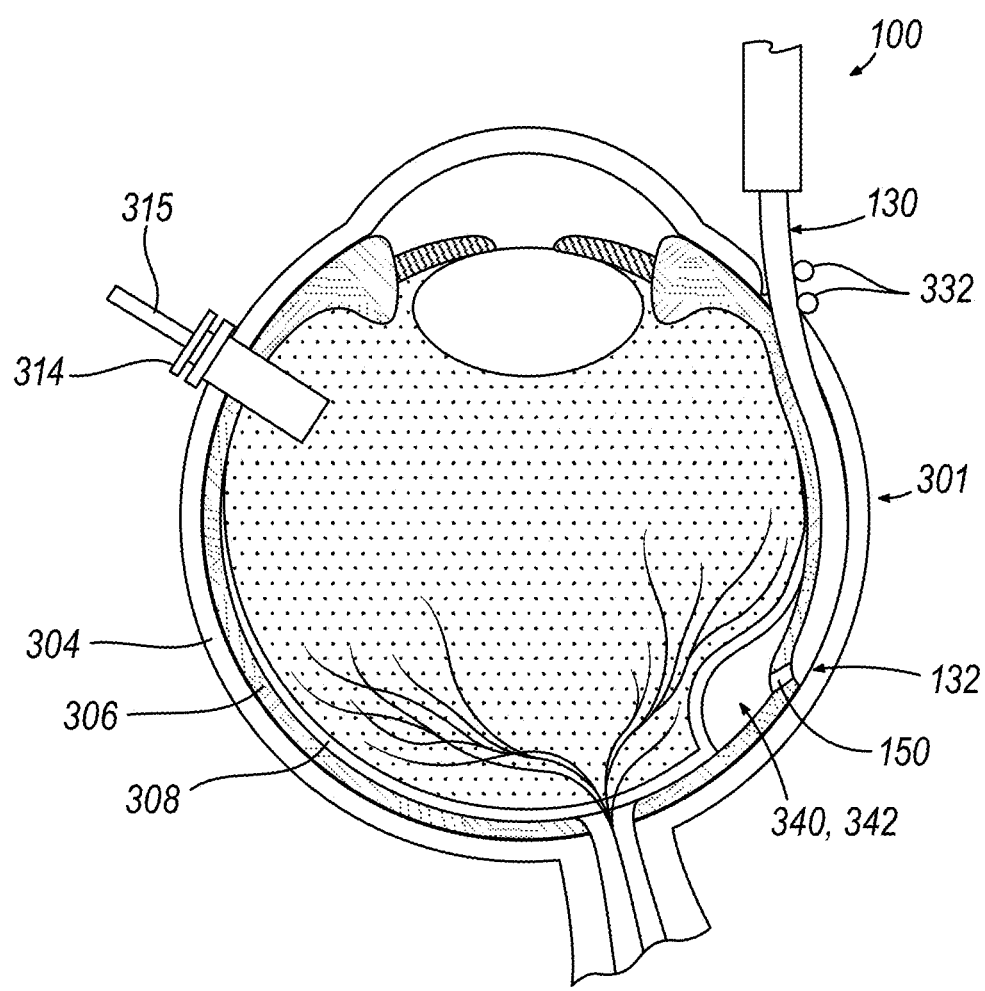
FIG. 4G depicts a cross-sectional side view of the eye of FIG. 4A, with the needle of FIG. 2B dispensing a therapeutic agent between a region of the retina and the choroid at the target location.

In the present example, the amount of therapeutic agent (342) that is ultimately delivered to the delivery site is approximately 50 μL, although any other suitable amount may be delivered. In some versions, a foot pedal is actuated in order to drive agent (342) out from needle (150). Alternatively, other suitable features that may be used to drive agent (342) out from needle (150) will be apparent to those skilled in the art in view of the teachings herein. Delivery of therapeutic agent (342) may be visualized by an expansion of the pocket of fluid as can be seen in FIG. 4G. As shown, therapeutic agent (342) essentially mixes with the fluid of leading bleb (340) as therapeutic agent (342) is injected into the subretinal space.

Once delivery is complete, needle (150) may be retracted by rotating knob (120) in a direction opposite to that used to advance needle (150); and cannula (130) may then be withdrawn from eye (301). Because of the size of needle (150), the site where needle (150) penetrated through choroid (306) is self-sealing, such that no further steps need be taken to seal the delivery site through choroid (306). Suture loop assembly (332) and chandelier (314) may be removed, and the incision in the sclera (304) may be closed using any suitable conventional techniques.

As noted above, the foregoing procedure may be carried out to treat a patient having macular degeneration. In some such instances, the therapeutic agent (342) that is delivered by needle (150) may comprise cells that are derived from postpartum umbilicus and placenta. As noted above, and by way of example only, the therapeutic agent (342) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, needle (150) may be used to deliver any other suitable substance or substances, in addition to or in lieu of those described in U.S. Pat. No. 7,413,734 and/or elsewhere herein. By way of example only, therapeutic agent (342) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

The procedure described above may be carried out in accordance with any of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein).

III. Example of Dose Clip for Syringe to Deliver Fluid to Subretinal Space

Those skilled in the art will recognize that it may be critical to ensure that an appropriate amount of fluid is delivered to the subretinal space of the eye (301), particularly in view of the anatomical constraints of the subretinal space. In the case of leading bleb (340) and therapeutic agent (342), delivering too much fluid may result in an undesirable degree of detachment of the retina (308) from the choroid (306); perhaps even to the point of the retina (308) rupturing. In the case of leading bleb (340), delivering too little fluid may result in insufficient separation of the retina (308) from the choroid (306), which may result in inadequate efficacy of subsequently delivered therapeutic agent (342). Similarly, delivering too little therapeutic agent (342) may fail to yield the desired therapeutic effect.

While many surgeons and their assistants may have substantial skill in ensuring that an appropriate amount of fluid is loaded in a syringe (50) before use of the syringe (50) to deliver the fluid, it may be desirable to provide a device that reliably and consistently ensures that the appropriate amount of fluid is loaded in a syringe (50) before use of the syringe (50) to deliver the fluid, such that a patient need not rely so much on the personal skill of the surgeon, etc. to only load the appropriate amount of fluid in the syringe (50). The following describes an example of a dose clip assembly (400) that may be used with a conventional syringe, such as syringe (50), to consistently provide precision and accuracy in the amount of fluid that is loaded into the syringe; which may in turn consistently provide precision and accuracy in the amount of fluid that is delivered to the subretinal space as part of the procedure described above with reference to FIGS. 3-4G.

Figure 5:
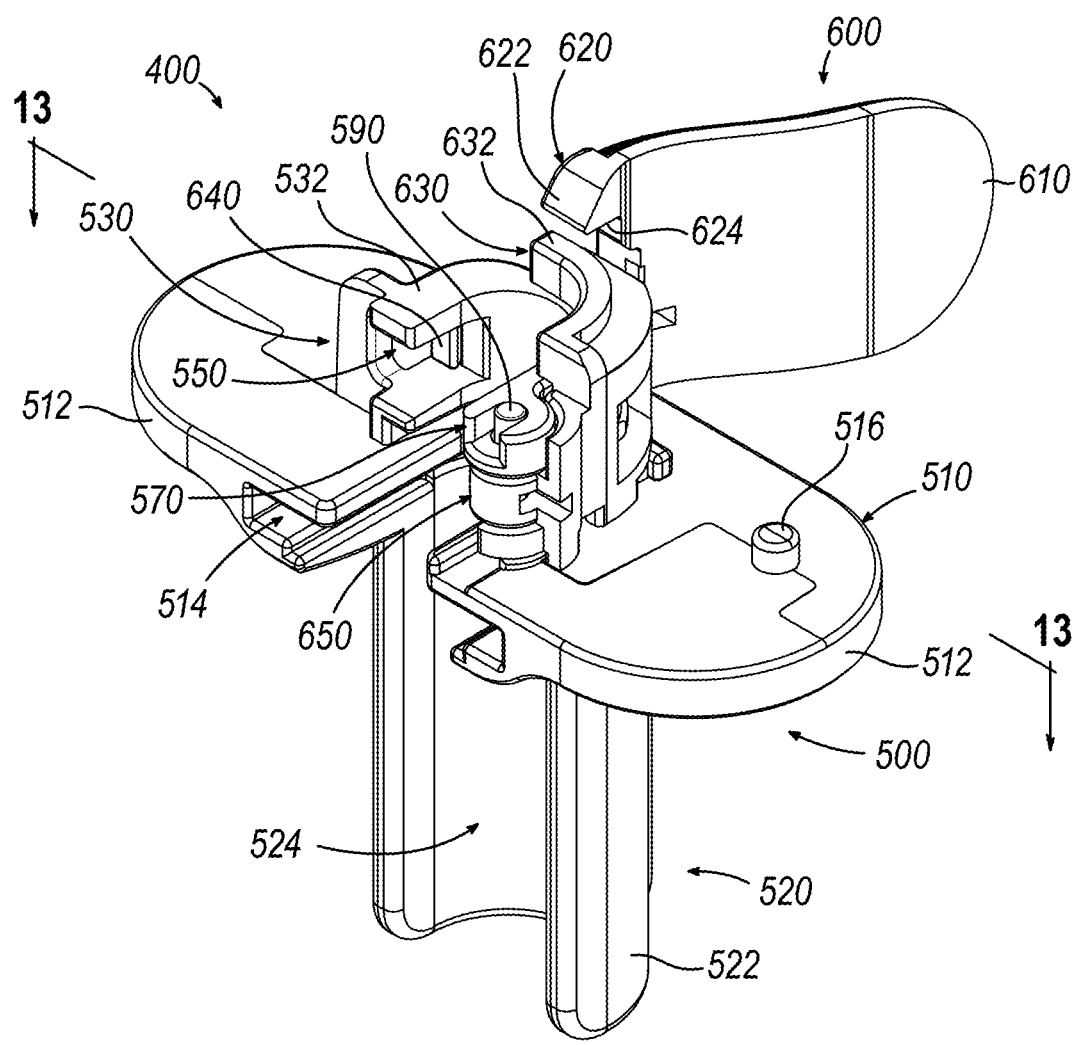
FIG. 5 depicts a perspective view of an example of a dose clip assembly for use with a syringe.
Figure 6:
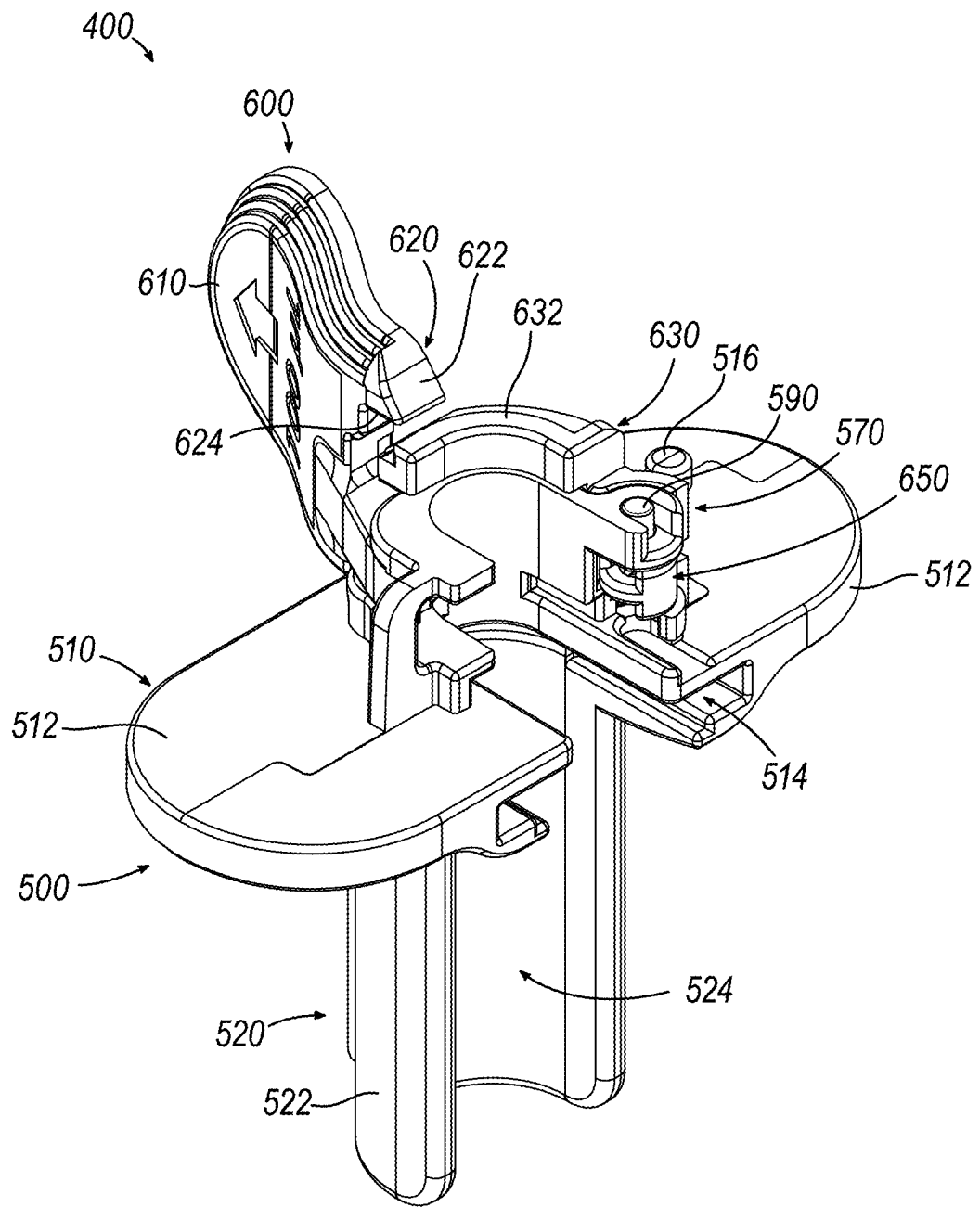
FIG. 6 depicts another perspective view of the dose clip assembly of FIG. 5.
Figure 7:
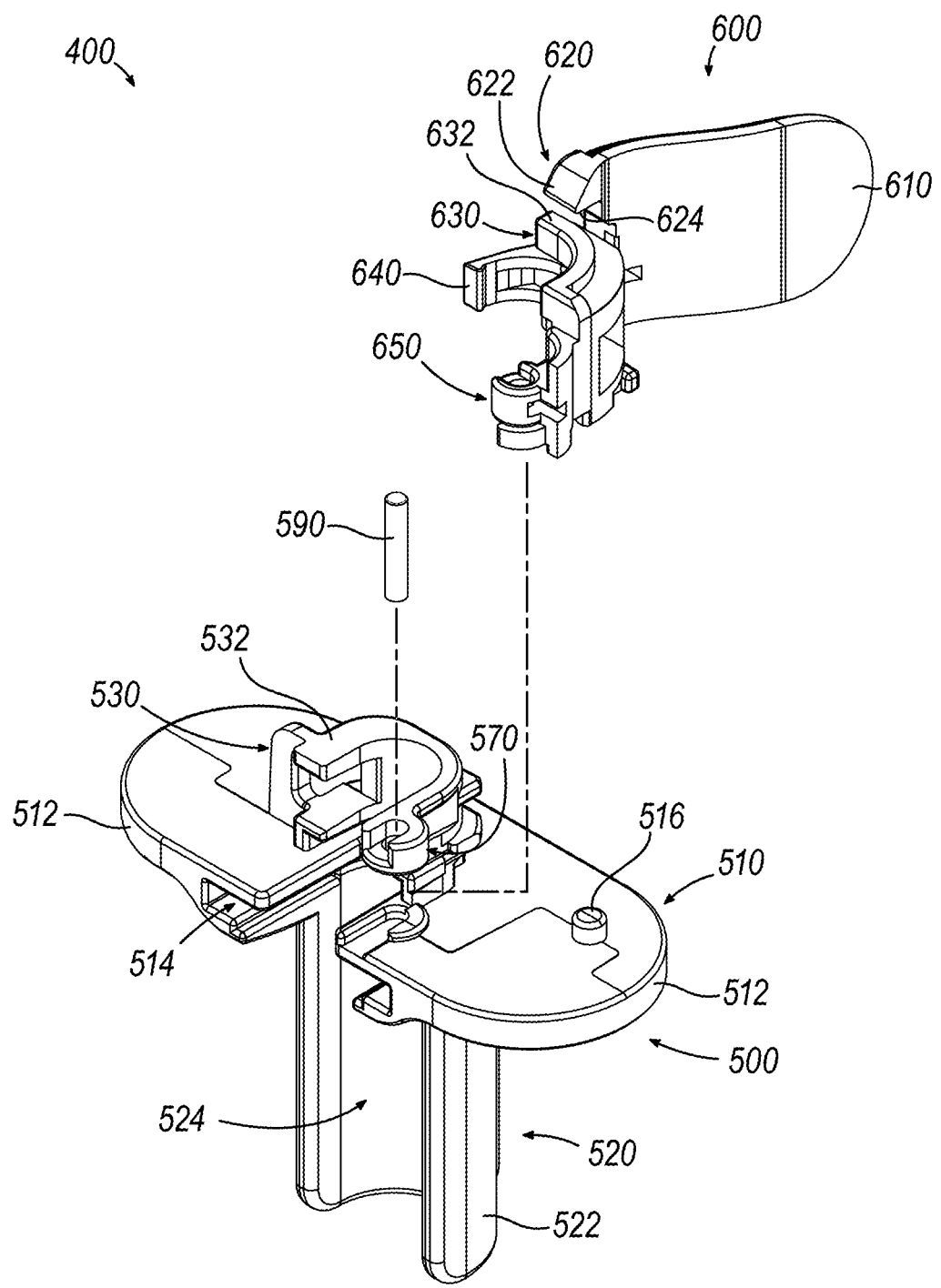
FIG. 7 depicts an exploded perspective view of the dose clip assembly of FIG. 5.
Figure 10:
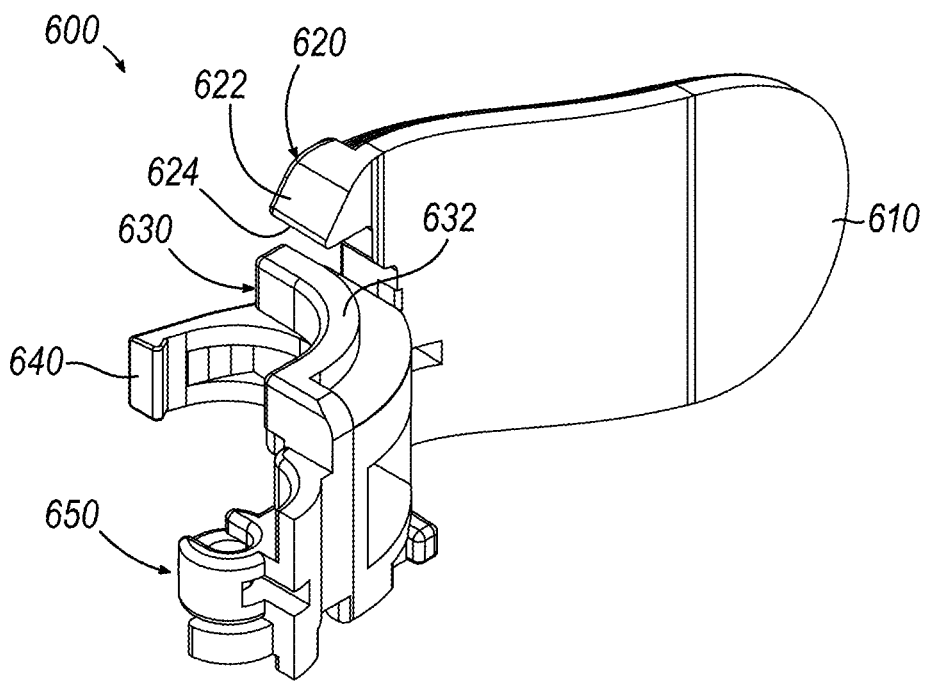
FIG. 10 depicts a perspective view of an upper member of the dose clip assembly of FIG. 5.
Figure 11:
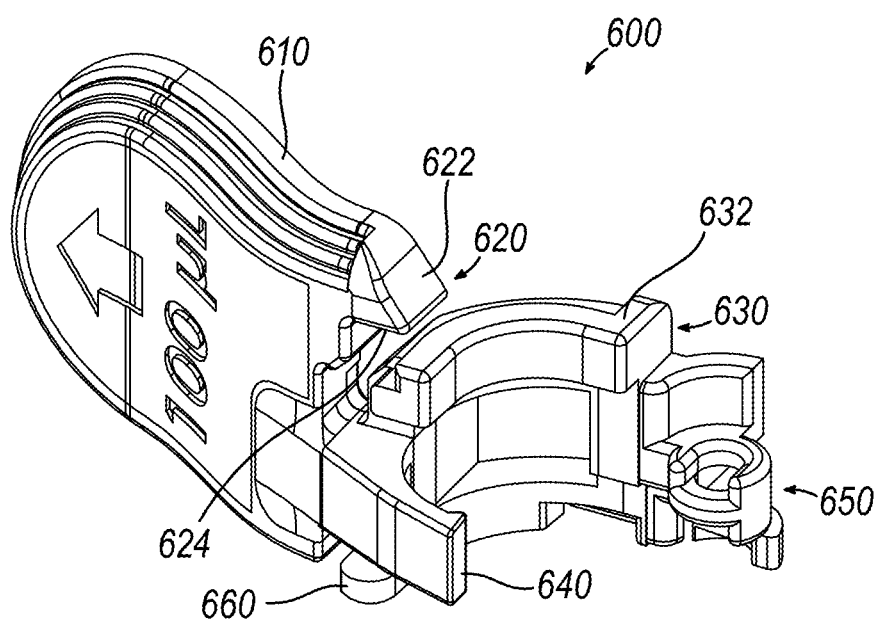
FIG. 11 depicts another perspective view of the upper member of FIG. 10.

As shown in FIGS. 5-7, dose clip assembly (400) of the present example includes a lower member (500) and an upper member (600). Lower and upper members (500, 600) are pivotably coupled together via a pin (590). As shown in FIGS. 5-9, lower member (500) includes a hilt portion (510) and a barrel portion (520). Hilt portion (510) is oriented perpendicularly relative to barrel portion (520). Hilt portion (510) includes a pair of outwardly protruding finger flanges (512) and defines a slot (514). A boss (516) extends upwardly and unitarily from one of the finger flanges (512). Barrel portion (520) includes an elongate, cylindraceous body (522) that defines a laterally presented recess (524). As described in greater detail below, recess (524) is configured to receive a barrel (710) of a syringe (700); while slot (514) is configured to receive a finger flange (712) of the syringe (700).

A plunger stop portion (530) protrudes upwardly from hilt portion (510). As best seen in FIGS. 8-9, plunger stop portion (530) includes an upwardly presented plunger stop surface (532), a latch receiving notch (550) with a latch edge (552), and a pin receiving structure (570). As will be described in greater detail below, plunger stop surface (532) is configured to arrest advancement of a thumb flange (722) of a plunger (720) of syringe (700). As will also be described in greater detail below, latch receiving notch (550) is configured to receive a latch arm (640) of upper member (600), with latch edge (522) providing engagement with latch arm (640) to thereby retain the pivotal position of upper member (600) relative to lower member (500).

In the present example, lower member (500) is formed of plastic, such that portions of recess (524) and/or slot (514) may deform to frictionally retain barrel (710) of syringe (700). Alternatively, lower member (500) may be formed of any other suitable material or combination of materials.

As shown in FIGS. 5-7 and 10-11, upper member (600) of the present example includes a tab (610), a plunger catch (620), a plunger stop portion (630), latch arm (640), and a pin receiving structure (650). Tab (610) extends laterally relative to the longitudinal axis defined by barrel portion (520) of lower member (500). Plunger catch (620) includes a ramp surface (622) and a lower surface (624). Plunger stop portion (630) includes an upwardly presented plunger stop surface (632). As will be described in greater detail below, plunger stop surface (632) is configured to arrest advancement of a thumb flange (722) of a plunger (720) of syringe (700). As will also be described in greater detail below, lower surface (624) of plunger catch (620) is configured to prevent proximal retraction of plunger (720) relative to barrel (710) (e.g., as may otherwise be caused from back pressure in fluid contained within barrel (710)). As noted above, latch arm (640) is configured to engage latch edge (522) of latch receiving notch (550) of lower member (500) to thereby retain the pivotal position of upper member (600) relative to lower member (500).

In the present example, upper member (600) is formed of plastic, such that at least a portion of upper member (600) may deform to accommodate a portion of thumb flange (722) between lower surface (624) of plunger catch (620) and plunger stop surface (632) of plunger stop portion (630). Alternatively, upper member (600) may be formed of any other suitable material or combination of materials.

Figure 12A:
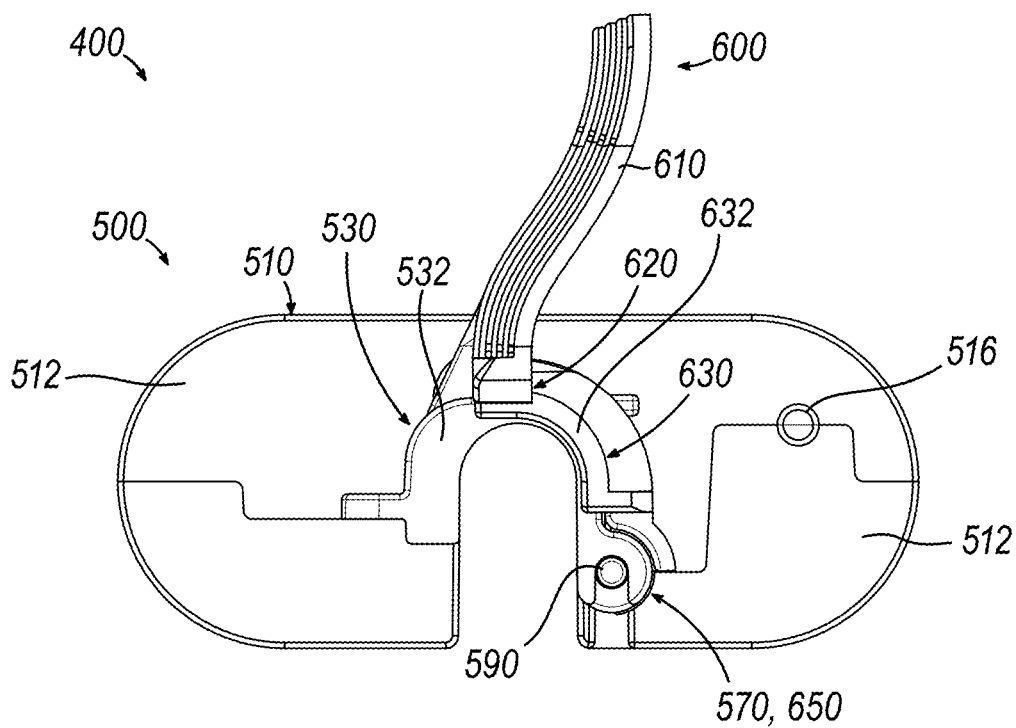
FIG. 12A depicts a top plan view of the dose clip assembly of FIG. 5, with the upper member in a first pivotal position relative to the lower member.
Figure 12B:
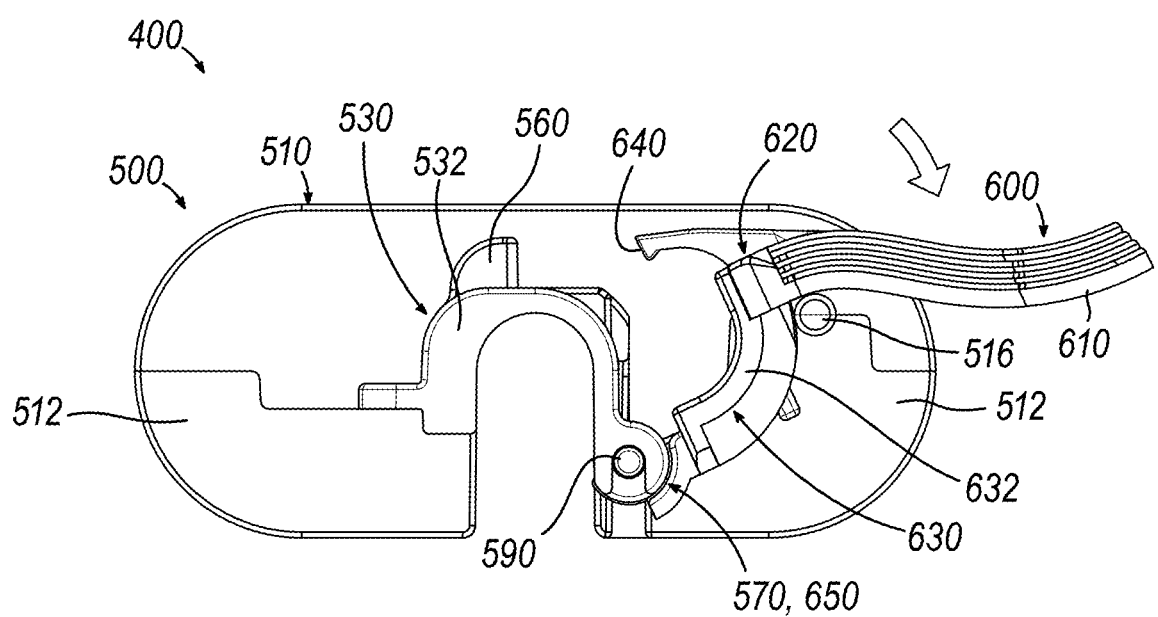
FIG. 12B depicts a top plan view of the dose clip assembly of FIG. 5, with the upper member in a second pivotal position relative to the lower member.

As noted above, lower and upper members (500, 600) are pivotally coupled together by pin (590), which is disposed in pin receiving structures (570, 650) of lower and upper members (500, 600). This coupling enables upper member (600) to pivot relative to lower member (500) between a first pivotal position (FIG. 12A) and a second pivotal position (FIG. 12B). When upper member (600) is in the first pivotal position relative to lower member (500), plunger stop portion (630) of upper member (600) is positioned over plunger stop portion (530) of lower member (500), such that plunger stop portion (630) will prevent thumb flange (722) from advancing further toward plunger stop portion (530). When upper member (600) is in the second pivotal position relative to lower member (500), plunger stop portion (630) of upper member (600) is positioned away from plunger stop portion (530) of lower member (500), such that plunger stop portion (630) will no longer prevent thumb flange (722) from advancing further toward plunger stop portion (530). In other words, the operator may freely advance plunger (720) relative to barrel (710) until thumb flange (722) reaches plunger stop surface (532) when upper member (500) is in the second pivotal position relative to lower member (600).

As best seen in FIG. 12B, boss (516) on hilt portion (510) of lower member (500) is configured to engage tab (610) and thereby arrest pivotal movement of upper member (600) once upper member (600) has reached the second pivotal position relative to lower member (500). Boss (516) is in the form of a peg that is integral with one of the finger flanges (512) of hilt portion (510) in this example. Alternatively, any other suitable kinds of structures may be used to arrest pivotal movement of upper member (600) relative to lower member (500) as will be apparent to those skilled in the art in view of the teachings herein. Boss (516) is merely optional.

As also noted above, and as best seen in FIG. 13, latch arm (640) is configured to engage latch edge (522) when upper member (600) is in the first pivotal position relative to lower member (500). This engagement between latch arm (640) and latch edge (522) will substantially maintain the pivotal position of upper member (600) relative to lower member (500), thereby substantially preventing inadvertent pivotal movement of upper member (600) relative to lower member (500). However, when an operator wishes to pivot upper member (600) from the first pivotal position (FIG. 12A) to the second pivotal position (FIG. 12B), latch arm (640) will sufficiently deform to allow latch arm (640) to clear latch edge (552), thereby allowing upper member (600) to pivot to the second pivotal position. In some versions, at least a portion of latch arm (640) is formed of a resilient material, such that latch arm (640) may repeatedly transition between a latched state and an unlatched state as upper member (600) is repeatedly pivoted between the first pivotal position and the second pivotal position. In some other versions, at least a portion of latch arm (640) (or a portion of latch edge (552)) is formed of a frangible material, such that latch arm (640) and latch edge (552) may no longer achieve a latching relationship after upper member (600) has been pivoted from the first pivotal position to the second pivotal position.

FIGS. 14A-14G show an example of dose clip assembly (400) being used with a syringe (700). Syringe (700) of this example includes barrel (710) and plunger (720). Barrel (710) includes finger flange (712). Plunger (720) includes thumb flange (722) at one end of a shaft (724) and a piston (726) on the other end of shaft (724). Piston (726) is sealingly disposed in barrel (710), such that the longitudinal position of piston (726) within barrel (710) may be varied to selectively vary the effective internal capacity of barrel (710), which will in turn influence the volume of fluid contained within barrel (710).

Figure 14A:
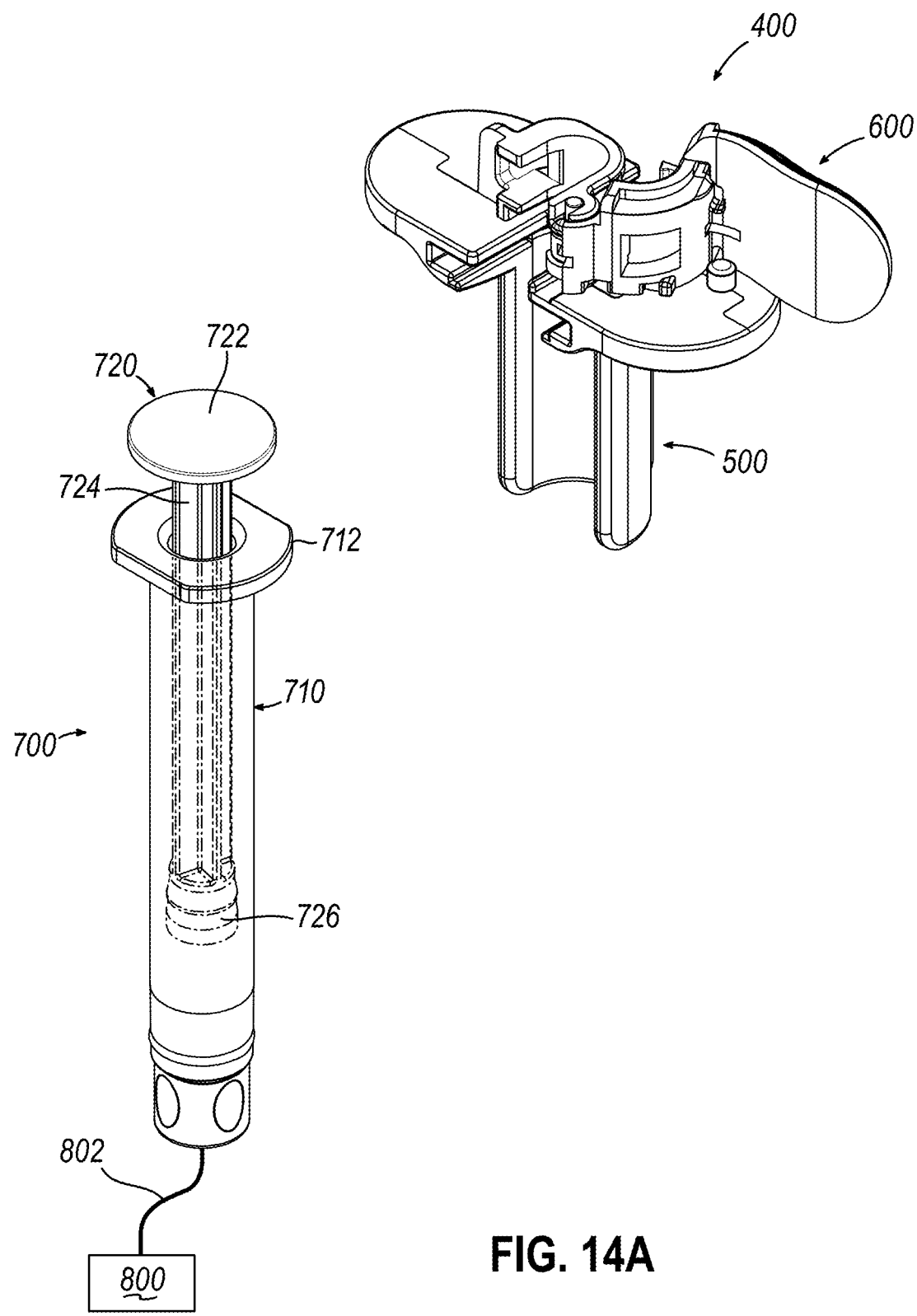
FIG. 14A depicts a perspective view of the dose clip assembly of FIG. 5 and a syringe, with the syringe being separated from the dose clip assembly, and with the syringe being coupled with a fluid source.

As shown in FIG. 14A, barrel (710) is initially coupled with a fluid source (800) via a conduit (802). In some instances, fluid source (800) contains leading bleb (340) fluid. In some other instances, fluid source (800) contains therapeutic agent (342) fluid. When barrel (710) is initially coupled with fluid source (800), plunger (720) is in a distal position relative to barrel (710). Also when barrel (710) is initially coupled with fluid source (800), syringe (700) is completely decoupled from dose clip assembly (400) in this example.

Figure 14B:
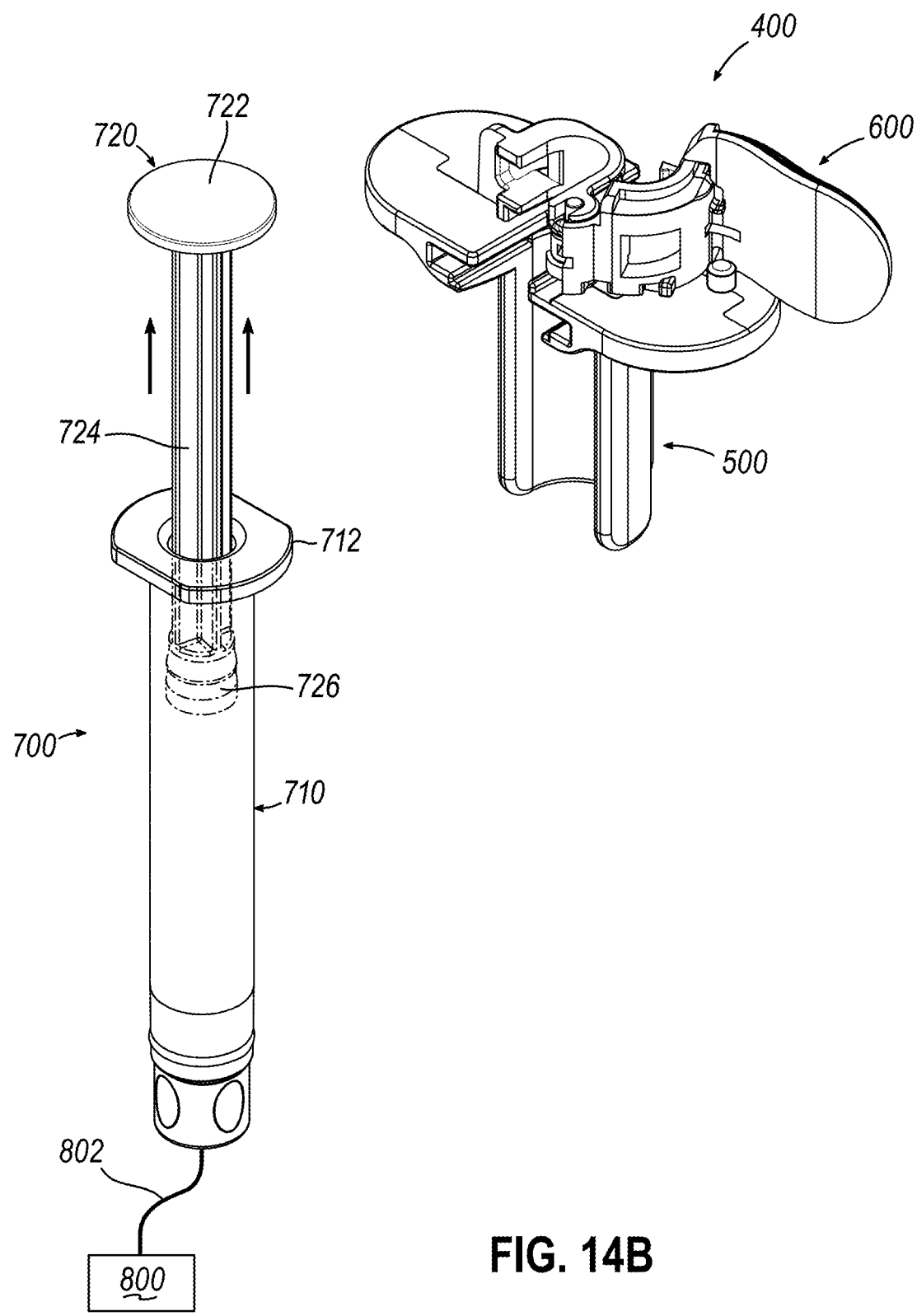
FIG. 14B depicts a perspective view of the dose clip assembly of FIG. 5 and the syringe of FIG. 14A, with the syringe being separated from the dose clip assembly, and with the syringe having drawn fluid from the fluid source.

With barrel (710) sufficiently coupled with fluid source (800), the operator retracts plunger (720) proximally relative to barrel (710) to the position shown in FIG. 14B. During such proximal retraction of plunger (720), syringe (700) draws a volume of fluid from fluid source (800) into barrel (710). This volume will be greater than the volume of fluid that will ultimately be delivered to the subretinal space of the eye (301).

Figure 14C:
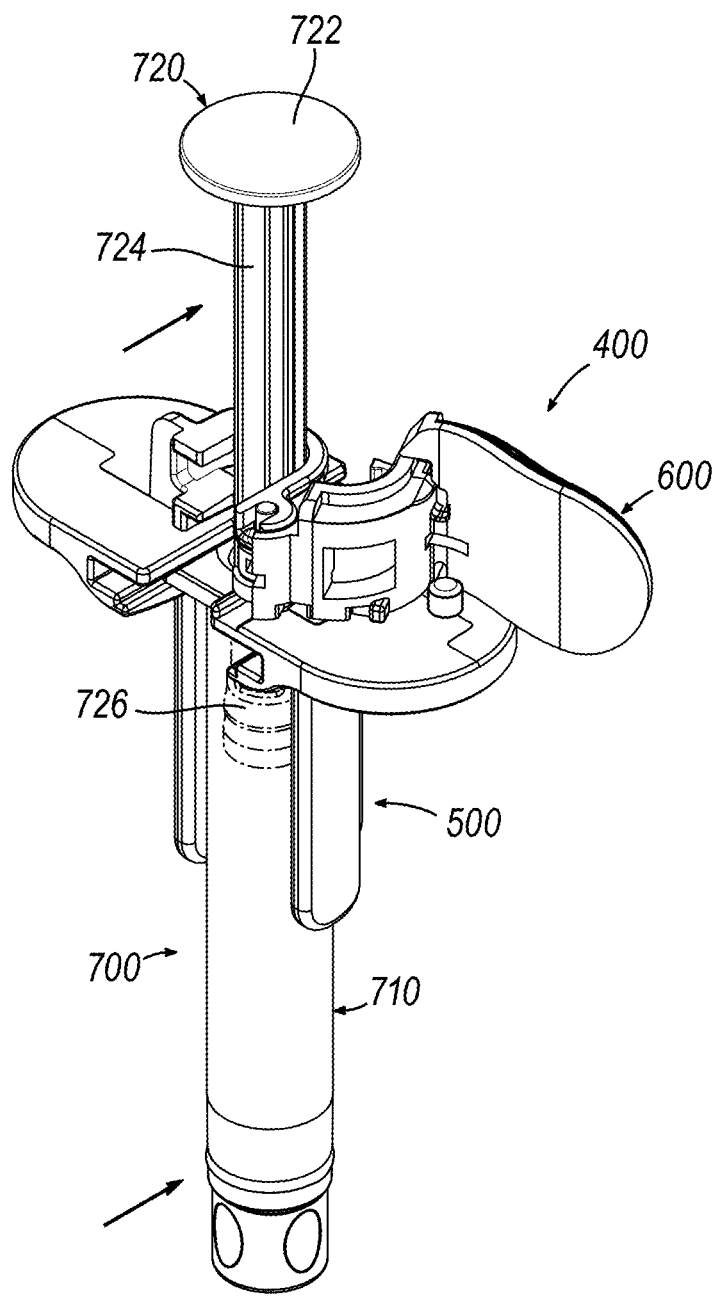
FIG. 14C depicts a perspective view of the dose clip assembly of FIG. 5 and the syringe of FIG. 14A, with the syringe being coupled with the dose clip assembly while holding the drawn fluid of FIG. 14B, and with the upper member of the dose clip assembly in the second pivotal position relative to the lower member of the dose clip assembly.

Once a volume of fluid has been drawn from fluid source (800) into barrel (710), syringe (700) is decoupled from fluid source (800) and coupled with dose clip assembly (400). In particular, as shown in FIG. 14C, barrel (710) is inserted into recess (524) of body (522); and finger flange (712) is inserted into slot (514). In some versions, recess (524) is configured to provide a snap fit with barrel (710) to thereby substantially retain barrel (710) in recess (524). In addition, or in the alternative, recess (524) may include one or more elastomeric features and/or other features that that are configured to grip or otherwise retain barrel (710). In addition, or in the alternative, slot (514) may include features that are configured to grip or otherwise retain finger flange (712). In the present example, at the stage shown in FIG. 14C, plunger (720) is still in the proximal position relative to barrel (710); and upper portion (600) is in the second pivotal position relative to lower portion (500). Alternatively, upper portion (600) may already be in the first pivotal position relative to lower portion (500) at this stage.

Figure 14D:
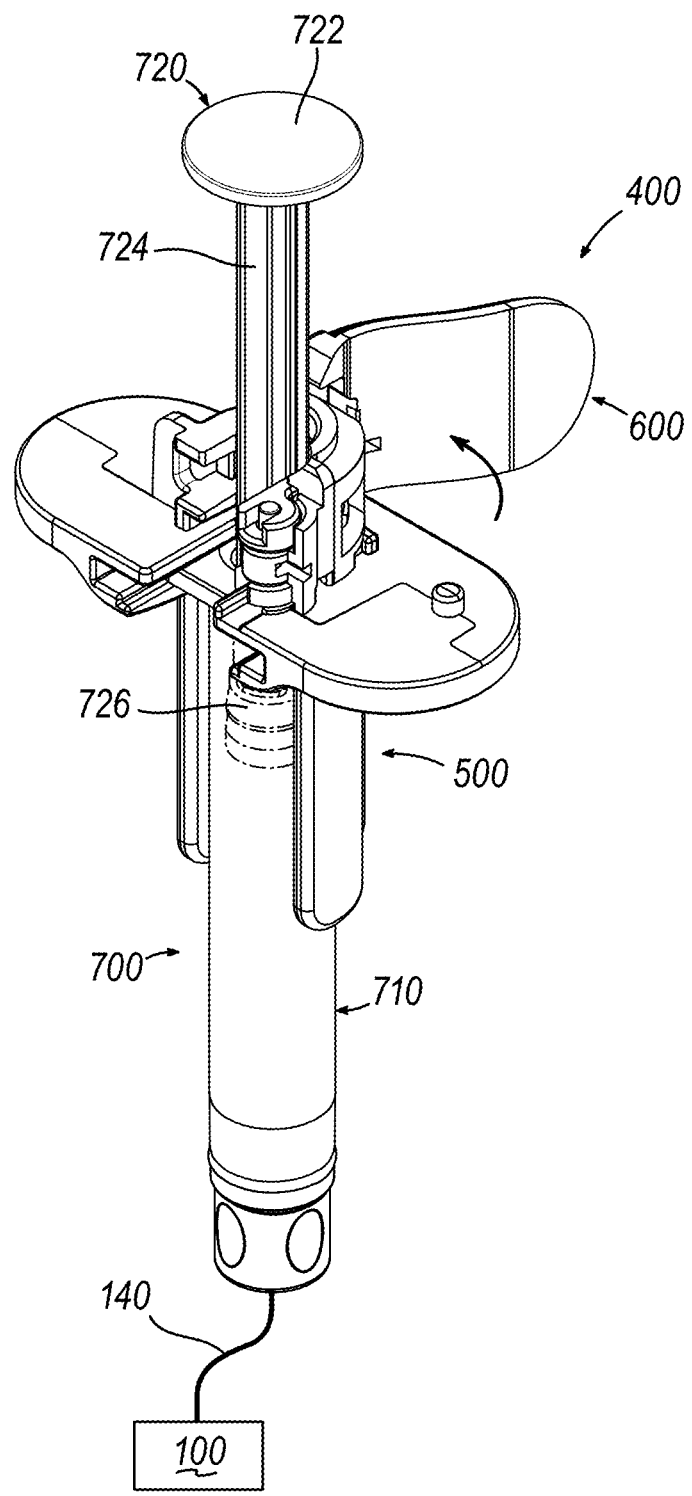
FIG. 14D depicts a perspective view of the dose clip assembly of FIG. 5 and the syringe of FIG. 14A, with the syringe being coupled with the dose clip assembly while holding the drawn fluid of FIG. 14B, with the upper member of the dose clip assembly in the first pivotal position relative to the lower member of the dose clip assembly, and with the syringe coupled with the instrument of FIG. 1.

Next, as shown in FIG. 14D, barrel (710) is coupled with instrument (100) via conduit assembly (140), both of which are described above. To the extent that upper portion (600) was not already be in the first pivotal position relative to lower portion (500) at this stage; upper portion (600) may be moved to the first pivotal position relative to lower portion (500) at this stage.

Figure 14E:
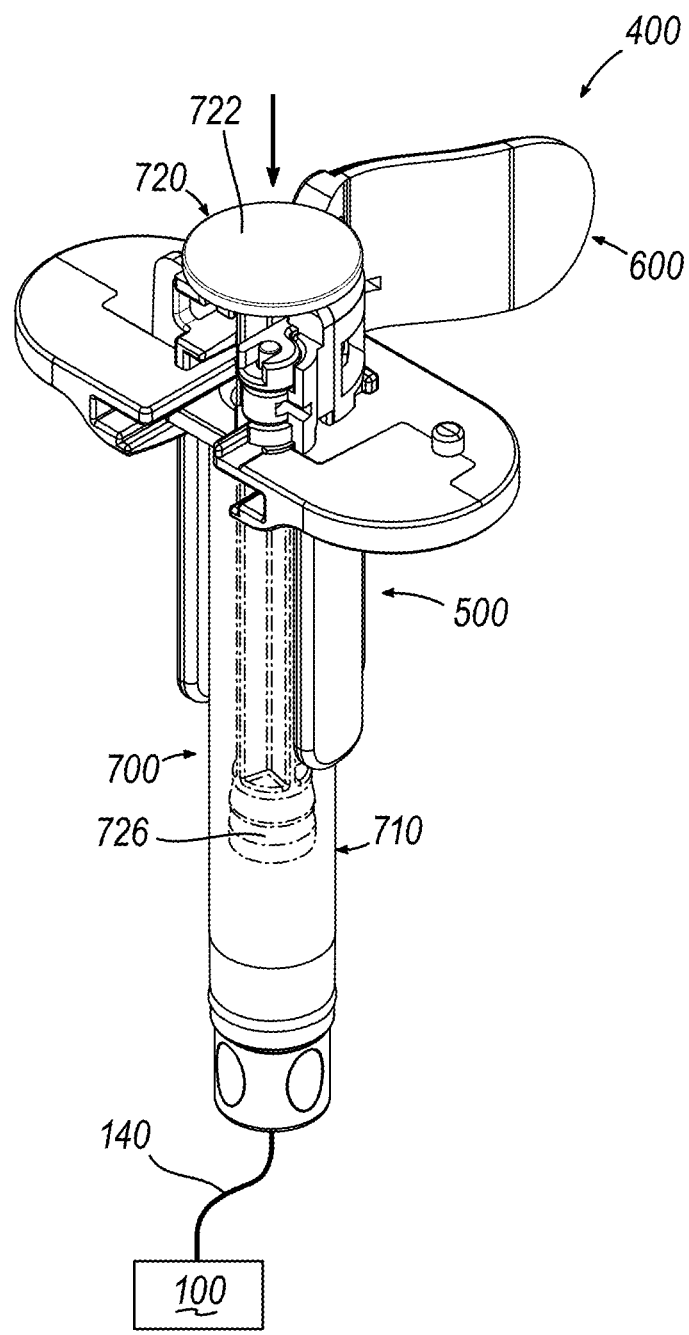
FIG. 14E depicts a perspective view of the dose clip assembly of FIG. 5 and the syringe of FIG. 14A, with the syringe being coupled with the dose clip assembly, with the upper member of the dose clip assembly in the first pivotal position relative to the lower member of the dose clip assembly, with the syringe coupled with the instrument of FIG. 1, and with the plunger of the syringe being advanced to a first longitudinal position relative to the barrel of the syringe.

After reaching the state shown in FIG. 14D, the operator may advance plunger (720) distally relative to barrel (710) until reaching the stage shown in FIG. 14E. This stage is also shown in stage 15A. At this stage, thumb flange (722) is captured between lower surface (624) of plunger catch (620) and plunger stop surface (632) of plunger stop portion (630). As plunger (720) transitions distally from the position shown in FIG. 14D to the position shown in FIG. 14E, thumb flange (722) eventually engages ramp surface (622) of plunger catch (620). This engagement between thumb flange (722) and ramp surface (622) may provide a camming effect that slightly deflects plunger catch (620) away from thumb flange (722) as thumb flange (722) traverses ramp surface (622). Once thumb flange (722) clears ramp surface (622), plunger catch (620) may snap back into place, such that lower surface (624) of plunger catch (650) is positioned over a corresponding region of thumb flange (722). In the present example, the engagement between latch arm (640) and latch edge (522) is strong enough to prevent upper member (600) from pivoting out of the first pivotal position relative to lower member (500) as thumb flange (722) traverses ramp surface (622).

Also during the transition from the state shown in FIG. 14D to the state shown in FIG. 14E, plunger (720) drives a portion of the fluid from barrel (710). This may in turn provide priming of conduit assembly (140) and instrument (100), purging any air from the fluid path between barrel (710) and the distal end of needle (150). Thus, during the transition from the state shown in FIG. 14D to the state shown in FIG. 14E, cannula (130) has not yet been inserted into the patient's eye (301).

Figure 15A:
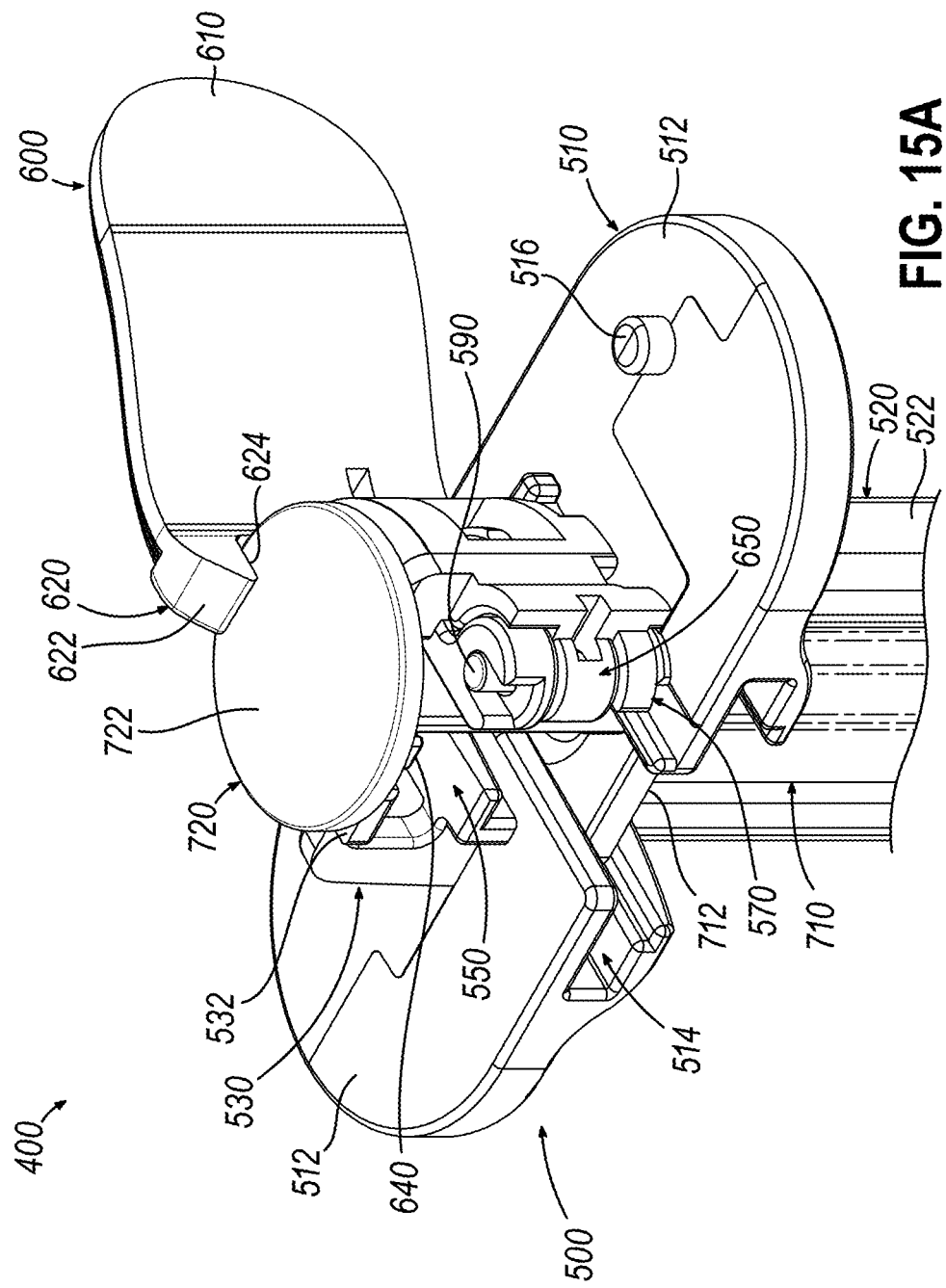
FIG. 15A depicts an enlarged perspective view of the dose clip assembly of FIG. 5 and the syringe of FIG. 14A in the operational state of FIG. 14E.

With thumb flange (722) captured between lower surface (624) of plunger catch (620) and plunger stop surface (632) of plunger stop portion (630) as shown in FIGS. 14E and 15A, plunger (720) may neither advance distally relative to barrel (710) nor retract proximally relative to barrel (710). Plunger stop portions (530, 630) thus cooperate to prevent plunger (720) from translating longitudinally relative to barrel (710) when dose clip assembly (400) and syringe (700) are in the state shown in FIGS. 14E and 15A. By preventing plunger (720) from translating distally relative to barrel (710), plunger stop portions (530, 630) prevent the inadvertent expulsion of fluid from barrel (710); thereby preventing the inadvertent expulsion of fluid from needle (150). By preventing plunger (720) from translating proximally relative to barrel (710), plunger stop portions (530, 630) prevent the inadvertent drawing of air or other fluid through needle (150), which might otherwise occur when back-pressure is inadvertently induced in the fluid line between the distal end of needle (150) and barrel (710). Thus, by preventing any longitudinal movement of plunger (720) relative to barrel (710), plunger stop portions (530, 630) cooperate to maintain a predetermined volume of fluid in barrel (710) and the entire fluid path between barrel (710) and the distal end of needle (150).

Figure 14F:
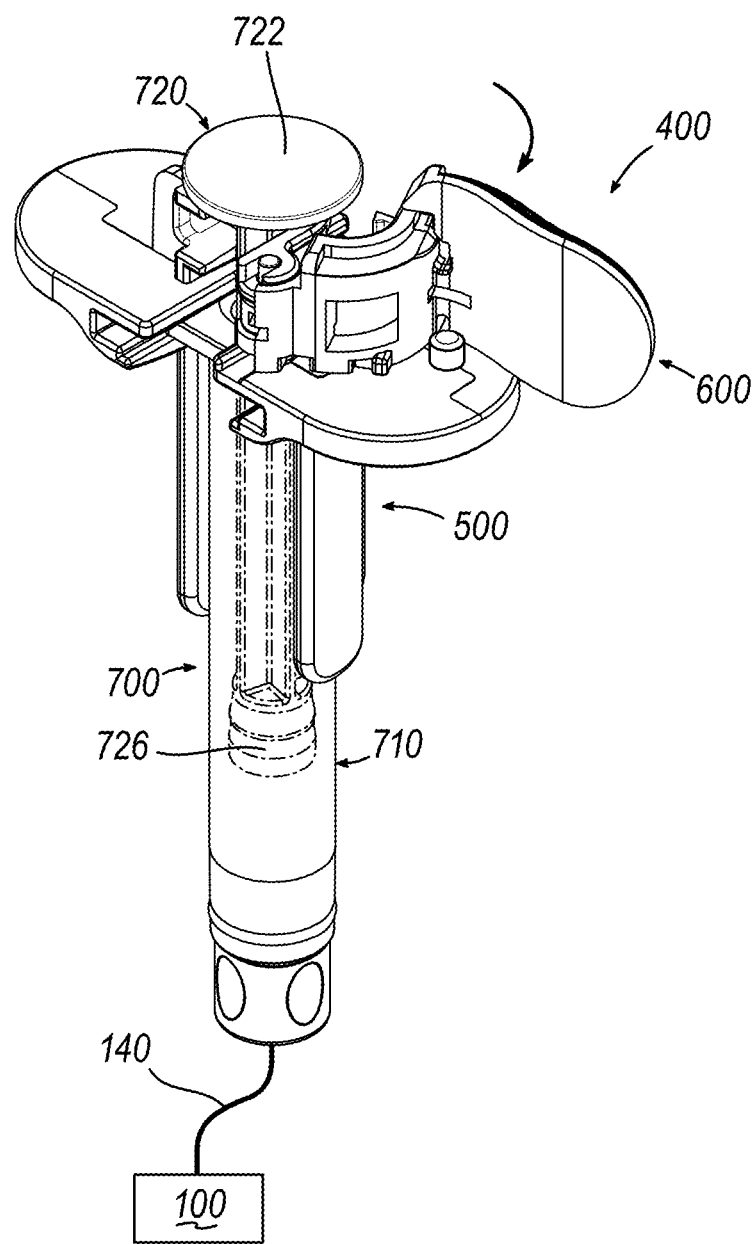
FIG. 14F depicts a perspective view of the dose clip assembly of FIG. 5 and the syringe of FIG. 14A, with the syringe being coupled with the dose clip assembly, with the upper member of the dose clip assembly in the second pivotal position relative to the lower member of the dose clip assembly, with the syringe coupled with the instrument of FIG. 1, and with the plunger of the syringe remaining in the first longitudinal position relative to the barrel of the syringe.

After achieving the state shown in FIGS. 14E and 15A, the operator may complete the steps shown in FIGS. 4A-4E and described above. In this example, barrel (710) contains the fluid to form leading bleb (340). In order to ready dose clip assembly (400) for delivery of leading bleb (340), the operator may pivot upper member (600) relative to lower member (500) to the second position as shown in FIG. 14F. This may be done by engaging tab (610) with the thumb of the same hand that is grasping body (522) of barrel portion (520). Thus, the operator may readily transition dose clip assembly (400) from the state shown in FIG. 14E to the state shown in FIG. 14F using just one single hand. During the transition from the state shown in FIG. 14E to the state shown in FIG. 14F, latch arm (640) may resiliently deform to disengage latch edge (522). Also during the transition from the state shown in FIG. 14E to the state shown in FIG. 14F, plunger stop surface (632) is no longer positioned under thumb flange (722) of plunger (720). Thus, with dose clip assembly (400) in the state shown in FIG. 14F, plunger (720) is free to advance distally relative to barrel (710) from the longitudinal position shown in FIG. 14F. In some cases, the operator refrains from pivoting upper member (600) from the first position shown in FIG. 14E to the second position shown in FIG. 14F until after reaching the stage of the procedure shown in FIG. 4E.

Figure 14G:
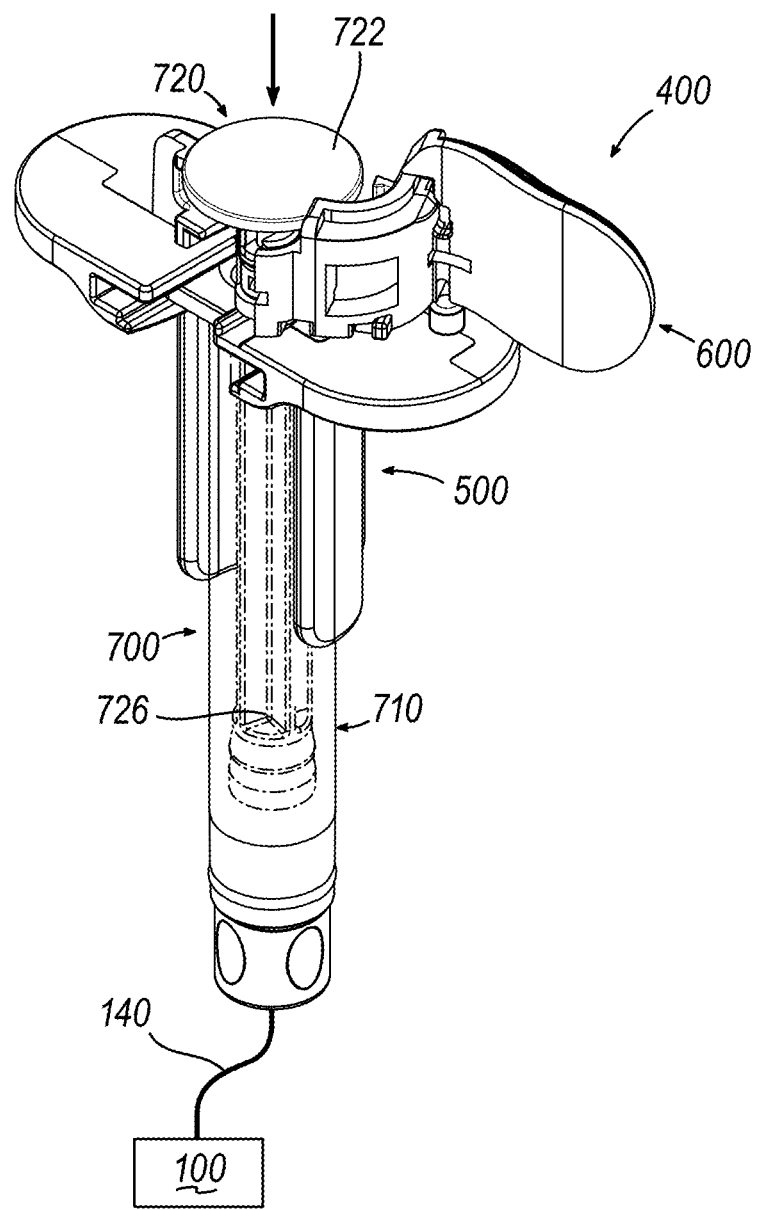
FIG. 14G depicts a perspective view of the dose clip assembly of FIG. 5 and the syringe of FIG. 14A, with the syringe being coupled with the dose clip assembly, with the upper member of the dose clip assembly in the second pivotal position relative to the lower member of the dose clip assembly, with the syringe coupled with the instrument of FIG. 1, and with the plunger of the syringe remaining in a second longitudinal position relative to the barrel of the syringe.
Figure 15B:
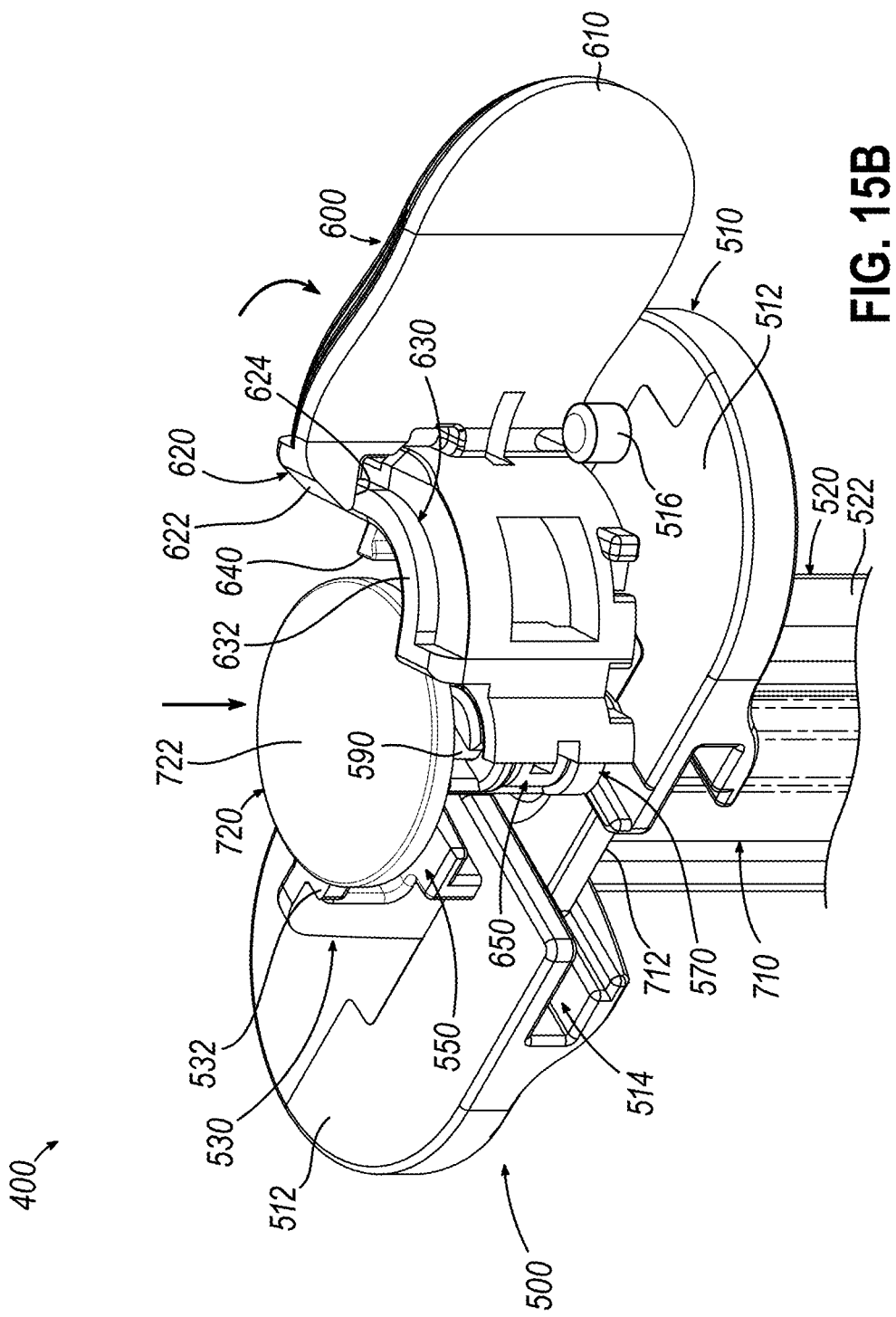
FIG. 15B depicts an enlarged perspective view of the dose clip assembly of FIG. 5 and the syringe of FIG. 14A in the operational state of FIG. 14G.

Once needle (150) has traversed the choroid (306) and is positioned to deliver fluid to the subretinal space as shown in FIG. 4E, and upper member (600) has been pivoted to the second position as shown in FIG. 14F, the operator may advance plunger (720) distally relative to barrel (710) until thumb flange (722) engages plunger stop surface (532) of plunger stop portion (530) of lower member (500). This state is shown in FIGS. 14G and 15B. As plunger (720) travels from the longitudinal position shown in FIG. 14F to the longitudinal position shown in FIGS. 14G and 15B, plunger (720) drives a predetermined volume of fluid from barrel (710). This provides communication of fluid through conduit assembly (140) and associated components of instrument (100), ultimately resulting in delivery of leading bleb (340) as shown in FIG. 4F. The volume of fluid forming leading bleb (340) will be dictated by the vertical distance between plunger stop surface (632) of plunger stop portion (630) and plunger stop surface (532) of plunger stop portion (530). Since this vertical distance between surfaces (632, 532) is fixed and predetermined, dose clip assembly (400) will ensure that syringe (700) predictably delvers a precise, predetermined volume of fluid for leading bleb (340) on a consistent basis. By way of example only, the predetermined volume of fluid may range from approximately 50 microliters to approximately 300 microliters. In some versions, the predetermined volume of fluid is 100 microliters.

In some instances, a combination of a second dose clip assembly (400) and a second syringe (700) is also in fluid communication with conduit assembly (140), with the second syringe containing therapeutic agent (342). As noted above, both syringes (700) may be coupled with conduit assembly (140) via a "Y" fitting or any other suitable component(s) as will be apparent to those skilled in the art in view of the teachings herein. In such scenarios, the combination of the second dose clip assembly (400) and second syringe (700) may undergo the same steps described above with reference to FIGS. 14A-14G. However, the plunger (720) of the second syringe (700) would not be advanced from the position shown in FIG. 14F to the position shown in FIG. 14G until after the plunger (720) of the first syringe (700) had been advanced from the position shown in FIG. 14F to the position shown in FIG. 14G to thereby deliver leading bleb (340). In other words, the plunger (720) of the second syringe (700) would not be advanced from the position shown in FIG. 14F to the position shown in FIG. 14G to deliver therapeutic agent (342) to the subretinal space as shown in FIG. 4G until after leading bleb (340) had already been delivered as shown in FIG. 4F.

In cases where two separate combinations of a dose clip assembly (400) and syringe (700) are used—one for leading bleb (340) fluid and the other for therapeutic agent (342) fluid—the corresponding dose clip assemblies (400) may have slightly different upper members (600) to provide different predetermined volumes of delivered fluid. For instance, upper member (600) that is used with the syringe (700) containing fluid for leading bleb (340) may be configured provide delivery of a first predetermined volume of fluid; while upper member (600) that is used with the syringe (700) containing therapeutic agent (342) may be configured provide delivery of a second predetermined volume of fluid. These different upper members (600) may vary based on the vertical position of their corresponding plunger stop surfaces (632). In other words, different dose clip assemblies (400) may vary based on the vertical distance between plunger stop surfaces (532, 632). In addition to, or instead of, providing variation between this vertical distance by providing differently configured upper members (600), lower members (500) may also be modified to provide different vertical distances between plunger stop surfaces (532, 632).

As noted above, dose clip assembly (400) is configured to promote single-handed use. For instance, the combination of dose clip assembly (400) and syringe (700) may be operated through all of the stages shown in FIGS. 14C-14G with the operator only using one single hand that grasps the combination of dose clip assembly (400) and syringe (700). This may leave the operator's other hand free to manipulate actuation knob (120) or other components of instrument (100); or to perform other tasks. Moreover, since upper member (600) remains secured to lower member (500) after upper member (600) is pivoted from the first position shown in FIG. 14E to the second position shown in FIG. 14F, the operator does not need to utilize a second hand to dispose of upper member (600) after transitioning dose clip assembly (400) from the state shown in FIG. 14E to the state shown in FIG. 14F. This may further simplify disposal of dose clip assembly (400) after the medical procedure is complete, such that dose clip assembly (400) may simply be disposed of as a single unit rather than being in separate parts.

While the foregoing example provides use of the combination of dose clip assembly (400) and syringe (700) in an ocular procedure, the combination of dose clip assembly (400) and syringe (700) may be used in various other kinds of medical procedures involving other regions of a patient's anatomy other than the eye (301). It is therefore contemplated that the present invention is not necessarily limited to use in the ocular procedure shown in FIGS. 4A-4G and described above. Various other suitable scenarios in which dose clip assembly (400) may be used will be apparent to those skilled in the art in view of the teachings herein.

IV. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a first member, the first member being configured to receive a portion of a syringe barrel, the first member including a first stop surface configured to engage a portion of a plunger to thereby arrest longitudinal movement of the plunger relative to the syringe barrel; and (b) a second member, the second member being coupled with the first member, the second member including a second stop surface configured to engage the portion of a plunger to thereby arrest longitudinal movement of the plunger relative to the syringe barrel, the second stop surface being spaced apart from the first stop surface; the second member being operable to move relative to the first member from a first position to a second position, the second member being configured to remain coupled with the first member while in both the first position and the second position; the second stop surface being positioned to engage the portion of the plunger when the second member is in the first position, the second stop surface being further configured to prevent the portion of the plunger from reaching the first stop surface when the second member is in the first position; the second stop surface being positioned to not prevent the portion of the plunger from reaching the first stop surface when the second member is in the second position.

Example 2

The apparatus of Example 1, the first member comprising: (i) an elongate body portion, and (ii) a hilt portion extending transversely relative to the body portion.

Example 3

The apparatus of Example 2, the body portion defining a recess configured to receive the syringe barrel.

Example 4

The apparatus of Example 3, the body portion being configured to provide a snap fit with the syringe barrel.

Example 5

The apparatus of any one or more of Examples 2 through 4, the hilt portion including a slot configured to receive a finger flange of the syringe barrel.

Example 6

The apparatus of any one or more of Examples 2 through 5, the hilt portion including a plunger stop portion extending upwardly from the hilt portion, the body portion extending downwardly from the hilt portion, the plunger stop portion including the first stop surface.

Example 7

The apparatus of any one or more of Examples 1 through 6, the first stop surface being configured to arrest distal longitudinal movement of the plunger relative to the syringe barrel, the second stop surface being configured to arrest distal longitudinal movement of the plunger relative to the syringe barrel.

Example 8

The apparatus of any one or more of Examples 1 through 7, the second member being pivotably coupled with the first member, the second member being operable to pivot relative to the first member from the first position to the second position.

Example 9

The apparatus of Example 8, further comprising a pin, the pin pivotably coupling the second member with the first member.

Example 10

The apparatus of any one or more of Examples 1 through 9, the first and second stop surfaces being configured to engage a thumb flange of the plunger to thereby arrest longitudinal movement of the plunger relative to the syringe barrel.

Example 11

The apparatus of any one or more of Examples 1 through 10, the second stop surface being positioned proximally in relation to the first stop surface when the second member is in the first position.

Example 12

The apparatus of any one or more of Examples 1 through 11, the second stop surface being positioned proximally in relation to the first stop surface when the second member is in the first position.

Example 13

The apparatus of Example 12, the second stop surface being positioned proximally in relation to the first stop surface by a distance from approximately 1 mm to approximately 7 mm when the second member is in the first position.

Example 14

The apparatus of any one or more of Examples 1 through 13, the second stop surface being positioned laterally in relation to the first stop surface when the second member is in the first position.

Example 15

The apparatus of any one or more of Examples 1 through 14, the second member further including a catch, the second member being configured to capture the portion of the plunger between the catch and the second stop surface when the second member is in the first position.

Example 16

The apparatus of Example 15, the catch including a lower surface, the lower surface being configured to abut an upper surface of a finger flange of the plunger when the second member is in the first position, the second stop surface being configured to abut a lower surface of the finger flange when the second member is in the first position.

Example 17

The apparatus of any one or more of Examples 1 through 16, further comprising a syringe, the syringe comprising: (i) a barrel coupled with the first member, and (ii) a plunger slidably disposed in the barrel.

Example 18

The apparatus of Example 17, further comprising a delivery instrument, the delivery instrument comprising: (i) a flexible cannula configured to fit between a choroid and sclera in a patient's eye, and (ii) a needle slidably disposed in the cannula, the needle defining a lumen in fluid communication with the barrel of the syringe.

Example 19

The apparatus of Example 18, the instrument further comprising an actuator operable to drive the needle longitudinally relative to the cannula, needle being configured to traverse the choroid to thereby deliver fluid from the syringe barrel to the subretinal space in the patient's eye.

Example 20

An apparatus, comprising: (a) a first member, the first member being configured to receive a portion of a syringe barrel, the first member including a first stop surface configured to engage a portion of a plunger to thereby arrest distal longitudinal movement of the plunger relative to the syringe barrel; and (b) a second member, the second member being coupled with the first member, the second member including: (i) a second stop surface configured to engage the portion of a plunger to thereby prevent distal longitudinal movement of the plunger relative to the syringe barrel, and (ii) a third stop surface configured to engage the portion of a plunger to thereby prevent proximal longitudinal movement of the plunger relative to the syringe barrel; the second member being operable to move relative to the first member from a first position to a second position; the second and third stop surfaces being positioned to engage the portion of the plunger when the second member is in the first position; the second stop surface being positioned to permit the portion of the plunger to reach the first stop surface when the second member is in the second position.

Example 21

The apparatus of Example 20, the second member being configured to remain coupled with the first member while in both the first position and the second position.

Example 22

A method comprising: (a) grasping an assembly, the assembly including: (i) a dose clip assembly, the dose clip assembly including: (1) a first member, (2) a second member coupled with the first member, and (ii) a syringe, the syringe including: (1) a barrel disposed, and (2) a plunger, the plunger being slidably disposed in the barrel; (b) retracting the plunger proximally relative to the barrel to thereby draw fluid from a fluid source into the barrel, the plunger being retracted to a first longitudinal position; (c) inserting the barrel of the syringe into the first member of the dose clip assembly; (d) decoupling the fluid source from the barrel; (e) with the barrel of the syringe disposed in the first member of the dose clip assembly, and with the second member being in a first position relative to the first member, advancing the plunger distally relative to the barrel to a second longitudinal position, the plunger engaging the second member in the second longitudinal position, the second member in the first position preventing further distal advancement of the plunger relative to the barrel; (f) moving the second member relative to the first member from the first position to a second position, the second member in the second position no longer preventing further distal advancement of the plunger relative to the barrel; and (g) with the second member in the second position, advancing the plunger distally relative to the barrel from the second longitudinal position to a third longitudinal position.

Example 23

The method of Example 22, the second member being in the second position during the act of inserting the barrel of the syringe into the first member of the dose clip assembly.

Example 24

The method of any one or more of Examples 22 through 23, further comprising coupling the barrel with a fluid delivery instrument.

Example 25

The method of Example 24, the act of coupling the barrel with a fluid delivery instrument being performed after the act of decoupling the fluid source from the barrel and before the act of advancing the plunger distally relative to the barrel to the second longitudinal position.

Example 26

The method of Example 25, the act of advancing the plunger distally relative to the barrel to the second longitudinal position providing a priming of a fluid path from the barrel to a fluid delivering portion of the fluid delivery instrument.

Example 27

The method of any one or more of Examples 22 through 26, after the act of advancing the plunger distally relative to the barrel to the second longitudinal position, the second member further preventing proximal retraction of the plunger relative to the barrel.

Example 28

The method of Example 27, the second member including a catch, the catch preventing proximal retraction of the plunger relative to the barrel.

Example 29

The method of Example 28, the act of act of advancing the plunger distally relative to the barrel to the second longitudinal position comprising traversing a cam surface of the catch with a portion of the plunger.

Example 30

The method of any one or more of Examples 22 through 29, the act of moving the second member relative to the first member from the first position to the second position comprising pivoting the second member relative to the first member.

Example 31

The method of Example 30, the second member remaining pivotably coupled with the first member after the act of moving the second member relative to the first member from the first position to the second position.

Example 32

The method of any one or more of Examples 30 through 31, the first member including a boss, the boss being configured to restrict pivotal movement of the second member relative to the first member, such that the boss arrests pivotal movement of the second member when the second member reaches the second position.

Example 33

The method of any one or more of Examples 22 through 32, further comprising moving the second member from the second position to the first position before performing the act of advancing the plunger distally relative to the barrel to the second longitudinal position.

Example 34

The method of any one or more of Examples 22 through 33, the first member arresting distal movement of the plunger upon the plunger reaching the third longitudinal position, such that the first member prevents further distal advancement of the plunger relative to the barrel.

Example 35

The method of any one or more of Examples 22 through 33, the act of retracting the plunger proximally relative to the barrel to thereby draw fluid from the fluid source into the barrel further comprising retracting the plunger from a fourth longitudinal position to the first longitudinal position.

Example 36

The method of Example 36, the fourth longitudinal position being distal to the third longitudinal position.

Example 37

The method of any one or more of Examples 22 through 36, the act of decoupling the fluid source from the barrel being performed before the act of inserting the barrel of the syringe into the first member of the dose clip assembly.

Example 38

The method of any one or more of Examples 22 through 37, the acts of moving the second member relative to the first member from the first position to the second position and advancing the plunger distally relative to the barrel from the second longitudinal position to the third longitudinal position being performed using only a single hand.

Example 39

The method of Example 38, the fingers of the single hand being used to grasp the first member during the acts of moving the second member relative to the first member from the first position to the second position and advancing the plunger distally relative to the barrel from the second longitudinal position to the third longitudinal position, the thumb of the single hand being used to move the second member relative to the first member from the first position to the second position.

Example 40

The method of any one or more of Examples 22 through 39, the fluid source comprising a fluid selected from the group consisting of a leading bleb fluid and therapeutic agent.

V. Miscellaneous

Any of the versions of the instruments described herein may include various other features in addition to or in lieu of those described above. By way of example only, any of the devices herein may also include one or more of the various features disclosed in any of the various references that are incorporated by reference herein.

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
    (a) a first member, the first member being configured to receive a portion of a syringe barrel, the first member including a first stop surface configured to engage a portion of a plunger to thereby arrest longitudinal movement of the plunger relative to the syringe barrel; and
    (b) a second member, the second member being coupled with the first member, the second member including a second stop surface configured to engage the portion of the plunger to thereby arrest longitudinal movement of the plunger relative to the syringe barrel, the second stop surface being spaced apart from the first stop surface;
    the second member being operable to move relative to the first member from a first position to a second position, the second member being configured to remain coupled with the first member while in both the first position and the second position;
    the second stop surface being positioned to engage the portion of the plunger when the second member is in the first position, the second stop surface being further configured to prevent the portion of the plunger from reaching the first stop surface when the second member is in the first position;

the second stop surface being positioned to not prevent the portion of the plunger from reaching the first stop surface when the second member is in the second position;

the second member further including a catch, the second member being configured to capture the portion of the plunger between the catch and the second stop surface when the second member is in the first position.

2. The apparatus of claim 1, the first member comprising:
(i) an elongate body portion, and
(ii) a hilt portion extending transversely relative to the elongate body portion.

3. The apparatus of claim 2, the elongate body portion defining a recess configured to receive the syringe barrel.

4. The apparatus of claim 3, the elongate body portion being configured to provide a snap fit with the syringe barrel.

5. The apparatus of claim 2, the hilt portion including a slot configured to receive a finger flange of the syringe barrel.

6. The apparatus of claim 2, the hilt portion including a plunger stop portion extending upwardly from the hilt portion, the elongate body portion extending downwardly from the hilt portion, the plunger stop portion including the first stop surface.

7. The apparatus of claim 1, the first stop surface being configured to arrest distal longitudinal movement of the plunger relative to the syringe barrel, the second stop surface being configured to arrest distal longitudinal movement of the plunger relative to the syringe barrel.

8. The apparatus of claim 1, the second member being pivotably coupled with the first member, the second member being operable to pivot relative to the first member from the first position to the second position.

9. The apparatus of claim 8, further comprising a pin, the pin pivotably coupling the second member with the first member.

10. The apparatus of claim 8, the first member being configured to orient the portion of the syringe barrel along a longitudinal axis, the second member being operable to pivot relative to the first member about a pivot axis from the first position to the second position, the pivot axis being parallel to the longitudinal axis.

11. The apparatus of claim 1, the first and second stop surfaces being configured to engage a thumb flange of the plunger to thereby arrest longitudinal movement of the plunger relative to the syringe barrel.

12. The apparatus of claim 1, the second stop surface being positioned proximally in relation to the first stop surface when the second member is in the first position.

13. The apparatus of claim 12, the second stop surface being positioned proximally in relation to the first stop surface by a distance from approximately 1 mm to approximately 7 mm when the second member is in the first position.

14. The apparatus of claim 1, the second stop surface being positioned laterally in relation to the first stop surface when the second member is in the first position.

15. The apparatus of claim 1, the catch including a lower surface, the lower surface being configured to abut an upper surface of a finger flange of the plunger when the second member is in the first position, the second stop surface being configured to abut a lower surface of the finger flange when the second member is in the first position.

16. The apparatus of claim 1, further comprising a syringe, the syringe comprising:
(i) a barrel coupled with the first member, and
(ii) a plunger slidably disposed in the barrel.

17. The apparatus of claim 16, further comprising a delivery instrument, the delivery instrument comprising:
(i) a flexible cannula configured to fit between a choroid and sclera in a patient's eye, and
(ii) a needle slidably disposed in the cannula, the needle defining a lumen in fluid communication with the barrel of the syringe.

18. The apparatus of claim 1, the catch being configured to prevent proximal longitudinal movement of the plunger relative to the syringe barrel when the second member is in the first position.

19. An apparatus, comprising:
(a) a first member, the first member being configured to receive a portion of a syringe barrel, the first member including a first stop surface configured to engage a portion of a plunger to thereby arrest longitudinal movement of the plunger relative to the syringe barrel; and
(b) a second member, the second member being coupled with the first member, the second member including a second stop surface configured to engage the portion of the plunger to thereby arrest longitudinal movement of the plunger relative to the syringe barrel, the second stop surface being spaced apart from the first stop surface;

the second member being operable to move relative to the first member from a first position to a second position, the second member being configured to remain coupled with the first member while in both the first position and the second position;

the second stop surface being positioned to engage the portion of the plunger when the second member is in the first position, the second stop surface being further configured to prevent the portion of the plunger from reaching the first stop surface when the second member is in the first position;

the second stop surface being positioned to not prevent the portion of the plunger from reaching the first stop surface when the second member is in the second position;

the second member being pivotably coupled with the first member, the second member being operable to pivot relative to the first member about a longitudinally-extending axis from the first position to the second position.

20. An apparatus, comprising:
(a) a first member, the first member being configured to receive a portion of a syringe barrel, the first member including a first stop surface configured to engage a portion of a plunger to thereby arrest movement of the plunger relative to the syringe barrel along a longitudinal axis; and
(b) a second member, the second member being coupled with the first member, the second member including a second stop surface configured to engage the portion of the plunger to thereby arrest movement of the plunger relative to the syringe barrel along the longitudinal axis, the second stop surface being spaced apart from the first stop surface;

the second member being operable to move relative to the first member from a first position to a second position, the second member being configured to remain coupled with the first member while in both the first position and the second position;

the second stop surface being positioned to engage the portion of the plunger when the second member is in the first position, the second stop surface being further configured to prevent the portion of the plunger from reaching the first stop surface when the second member is in the first position;

the second stop surface being positioned to not prevent the portion of the plunger from reaching the first stop surface when the second member is in the second position;

the second member being pivotably coupled with the first member, the second member being operable to pivot relative to the first member about a pivot axis from the first position to the second position, the pivot axis being parallel to the longitudinal axis.

* * * * *